United States Patent
Cossio Mora et al.

(10) Patent No.: US 8,835,659 B2
(45) Date of Patent: Sep. 16, 2014

(54) POLYSUBSTITUTED BENZOFURANS AND MEDICINAL APPLICATIONS THEREOF

(75) Inventors: Fernando Pedro Cossio Mora, San Sebastián (ES); Leire Lidia Arias Echeverría, San Sebastián (ES); Yosu Ion Vara Zalazar, San Sebastián-Gipuzkoa (ES); Eneko Aldaba Arévalo, San Sebastián-Gipuzkoa (ES); Eider San Sebastián Larzabal, San Sebastián-Gipuzkoa (ES); Aizpea Zubia Olascoaga, San Sebastián-Gipuzkoa (ES)

(73) Assignees: Ikerchem, S.L., San Sebastian-Gipuzkoa (ES); Universidad del Pais Vasco, Leioa-Vizcaya (ES)

( * ) Notice: Subject to any disclaimer, the term of this patent is extended or adjusted under 35 U.S.C. 154(b) by 0 days.

(21) Appl. No.: 13/695,971

(22) PCT Filed: May 10, 2011

(86) PCT No.: PCT/EP2011/057502
§ 371 (c)(1),
(2), (4) Date: Jan. 17, 2013

(87) PCT Pub. No.: WO2011/141458
PCT Pub. Date: Nov. 17, 2011

(65) Prior Publication Data
US 2013/0217730 A1    Aug. 22, 2013

(30) Foreign Application Priority Data

May 11, 2010  (EP) .................................. 10382116.1

(51) Int. Cl.
| | | |
|---|---|---|
| *C07D 307/00* | (2006.01) | |
| *C07D 307/87* | (2006.01) | |
| *C07D 307/93* | (2006.01) | |
| *C07D 317/00* | (2006.01) | |
| *C07D 323/02* | (2006.01) | |
| *A01N 43/08* | (2006.01) | |
| *A61K 31/34* | (2006.01) | |
| *C07D 307/81* | (2006.01) | |
| *C07D 307/82* | (2006.01) | |
| *C07D 307/92* | (2006.01) | |
| *C07D 405/04* | (2006.01) | |
| *C07D 407/04* | (2006.01) | |
| *C07D 307/79* | (2006.01) | |
| *C07D 307/80* | (2006.01) | |

(52) U.S. Cl.
CPC ............ *C07D 307/80* (2013.01); *C07D 307/81* (2013.01); *C07D 307/82* (2013.01); *C07D 307/92* (2013.01); *C07D 405/04* (2013.01); *C07D 407/04* (2013.01); *C07D 307/79* (2013.01)

USPC ........... 549/466; 549/462; 549/469; 549/429; 514/469; 514/470; 514/461; 514/468

(58) Field of Classification Search
USPC ......................... 546/284.1; 514/469; 549/466
See application file for complete search history.

(56) References Cited

U.S. PATENT DOCUMENTS

| | | |
|---|---|---|
| 2003/0149079 A1 | 8/2003 | Shimada et al. |
| 2009/0298905 A1* | 12/2009 | Cossio et al. ................. 514/415 |

FOREIGN PATENT DOCUMENTS

| | | |
|---|---|---|
| DE | 2909754 A1 | 9/1980 |
| EP | 1283208 A1 | 2/2003 |
| JP | 1213276 A | 8/1989 |
| WO | 2006094236 A1 | 9/2006 |
| WO | 2007019344 A1 | 2/2007 |
| WO | 2008108730 A1 | 9/2008 |

OTHER PUBLICATIONS

Minutola; J. Med. Chem. 2005, 48, 6783-6786.*
Wermuth; Practice of Medicinal Chemistry, Third Ed., 2008, Elsevier, Chapters 6 and 15.*
Fukai, T. et al.; "Cytotoxic activity of low molecular weight polyphenols against human oral tumor cell lines," Anticancer Research, 2000, pp. 2525-2536, vol. 20, Abstract Only.
Erber, S. et al.; "2-Phenylbenzo[b]furans: relationship between structure, estrogen receptor affinity and cytostatic activity against mammary tumor cells," Anti-Cancer Drug Design, 1991, pp. 417-426, vol. 6, Abstract Only.
Kim, Ikyon, et al.; "BCl3-promoted synthesis of benzofurans," Tetrahedron Letters, 2008, pp. 6579-6584, vol. 49.
Baziard-Mouysset, G. et al.; "Synthesis and calcium antagonistic activity of a series of diethyl benzofuryl, benzotheinyl and benzogammapyronyl benzylphosphonates," European Journal of Medicinal Chemistry, 1993, pp. 539-546, vol. 28.

(Continued)

*Primary Examiner* — John Mabry
*Assistant Examiner* — Daniel Carcanague
(74) *Attorney, Agent, or Firm* — Tristan A. Fuierer; Moore & Van Allen, PLLC

(57) ABSTRACT

The present invention refers to compounds of formula (I):

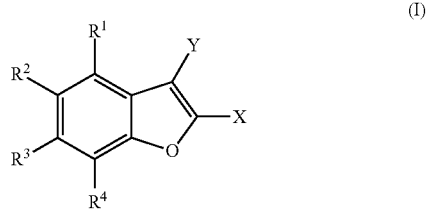

as well as to a method for their preparation, pharmaceutical compositions comprising the same, and use thereof for the treatment and/or chemoprevention of cancer, aging related diseases or processes, diabetes and neurodegenerative diseases.

7 Claims, 1 Drawing Sheet

(56) References Cited

OTHER PUBLICATIONS

Kato, K. et al.; Database Caplus, Chemical Abstract Service, XP002645362, STN accession No. 1990:98385, Database accession No. 112:98385, 1998, Abstract.
Sastraruji, Thanapat, et al.; "Phytochemical studies on *Stemona aphylla*: isolation of a new stemofoline alkaloid and six new stemofurans,", Journal of Natural Products, 2011, pp. 60-64, vol. 74, Abstract Only.
Duan, Xin-Fang, et al.; "A Facile Two-Step Synthesis of 2-Arylbenzofurans Based on the Selective Cross McMurry Couplings," Journal of Organic Chemistry, 2007, pp. 10283-10286, vol. 72.
International Search Report, Jul. 12, 2011.
Beilstein Database BRN 306250, XP-002590276, 1933, p. 374, Journal of Organic Chemistry.
Beilstein Database BRN 1684911, XP-002590277, 1967, pp. 1777-1784, Canadian Journal of Chemistry, vol. 45.
Beilstein Database BRN 5101440, XP-002590278, 1984, pp. 734-741, Liebigs Annalen der Chemie, vol. 4.
Beilstein Database BRN 10668512, XP-002590272, 2007, pp. 1616-1621, Bioorganic & Medicinal Chemistry, vol. 17.
Beilstein Database BRN 10677052, XP-002590275, 2006, pp. 5987-5990, Organic Letters, vol. 8.
Beilstein Database BRN 11060569, XP-002590274, 2006, pp. 1657-1662, Synlett, vol. 11.
Beilstein Database BRN11295947, XP-002590273, 2007, pp. 10283-10286, Journal of Organic Chemistry, vol. 72.
Zhang, Mi, et al.; "In vivo hypoglycemic effects of phenolics from the root bark of *Morus alba*," Fitoterapia, 2009, pp. 475-477, vol. 80.

* cited by examiner

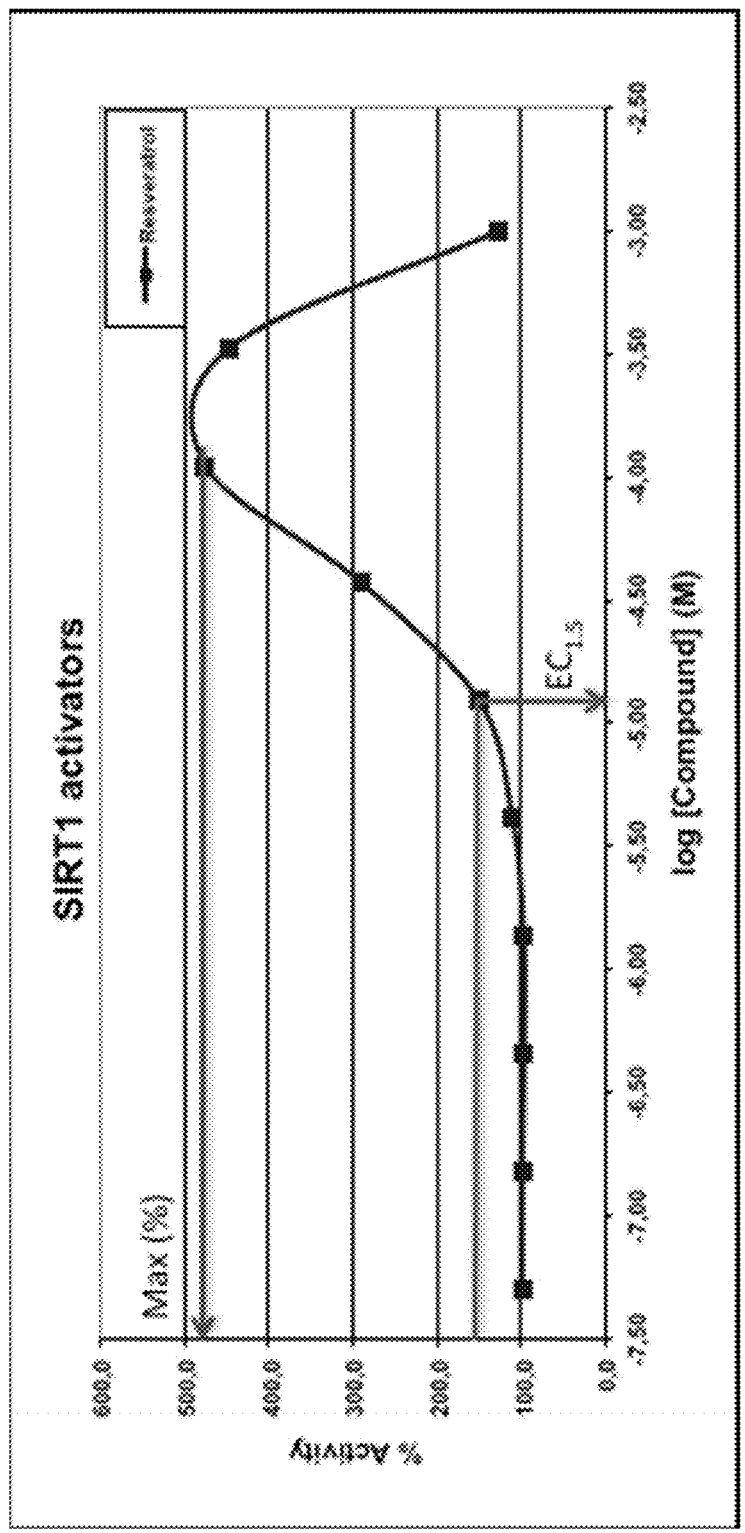

POLYSUBSTITUTED BENZOFURANS AND MEDICINAL APPLICATIONS THEREOF

CROSS-REFERENCE TO RELATED APPLICATIONS

This application is filed under the provisions of 35 U.S.C. §371 and claims the priority of International Patent Application No. PCT/EP2011/057502 filed on 10 May 2011 entitled "Polysubstituted Benzofurans and Medicinal Applications Thereof" in the name of Fernando Pedro COSSÍO MORA, et al., which claims priority to European Patent Application No. EP 10382116.1, filed on 11 May 2010, both of which are hereby incorporated by reference herein in their entirety.

FIELD OF THE INVENTION

The present invention is related to new compounds derived from polysubstituted benzofuran rings, with new processes for their preparation and use thereof for the treatment and/or chemoprevention of cancer, diabetes, aging related diseases or processes, or neurodegenerative diseases.

BACKGROUND OF THE INVENTION

Emerging literature indicates that mechanisms of aging and associated malignancies are intricately down-regulated both by calorie restriction regimens and calorie restriction mimetics, such as plant polyphenols. Among these natural polyphenols, one of the most studied is resveratrol, which is believed to modulate the activity of SIRT1, either directly, or indirectly via modulation of the activity of other enzymes and proteins such as the AMP-activated protein kinase (AMPK) (cf. D. Beher et al. *Chem. Biol. Drug Des.* 2009, 74, 619), the p70 ribosomal protein S6 kinase 1 (S6K1) (cf. S. M. Armour et al. *Aging* 2009, 1, 511) and integrin αv3 (cf. H. Y. Lin et al. *FASEB J.* 2006, 20, 1742). An increase in lifespan in *saccharomyces cerevisiae* through the administration of plant polyphenols has been described (cf. K. T. Howitz et al. *Nature* 2003, 425, 191), which could be related to the activation of sirtuins. Therefore, sirtuins constitute an important therapeutic target in many diseases associated with aging (cf. P. A. Cole *Nature Chem. Biol.* 2008, 4, 590; J. C. Milne, J. M. Denu *Curr. Op. Chem. Biol.* 2008, 12, 11).

As mentioned, one of the most studied plant polyphenol described to date is resveratrol, whose therapeutic potential is well documented through in vivo experiments (cf. J. A. Baur, D. A. Sinclair *Nature Rev. Drug Discovery* 2006, 5, 493). Thus, it has been described the ability of resveratrol to inhibit carcinogenesis in different stages (cf. M. Jang et al. *Science* 1997, 275, 218), all as chemoprevention by inhibiting cyclooxygenase and ornithine decarboxylase (cf. K. Subbaramaiah et al. *J. Biol. Chem.* 1998, 273, 21875), inhibition of angiogenesis (cf. S.-H. Tseng et al. *Clin. Cancer Res.,* 2004, 10, 2190) and metastasis (cf. Y. Kimura, H. Okuda *J. Nutr.* 2001, 131, 1844), as well as induction of alterations in the cell cycle and apoptosis (cf. B. B. Aggarwal et al. *Anticancer Res.* 2004, 24, 2783). It also has been demonstrated that resveratrol prevents cardiovascular diseases (cf. H.-F. Li, S.-A. Chen, S.-N. Wu *Cardiovasc. Res.* 2000, 45, 1035; S. Bradamante, L. Barenghi, A. Villa *Cardiovasc. Drug Rev.* 2004, 22, 169) and has anti-inflammatory (cf. D.-S. Jang et al. *Biochem. Pharmacol.* 1999, 57, 705) and neuroprotective activity (cf. Y. K. Gupta, S. Briyal, G. Chaudhary *Pharmacol. Biochem. Behav.* 2002, 71, 245).

In this line, resveratrol has been observed to play a key role in the protection of neurons from Huntington's diseases (HD), Alzheimer Disease (AD), Parkinson's Disease (PD), ischemic brain injury, seizures and epilepsy (cf. T. S. Anekonda *Brain Res. Rev.* 2006, 52, 316).

Briefly, resveratrol was observed to protect neurons against polyQ toxicity in a mouse model of Huntington's disease (cf. J. A. Parker et al. *Nat. Genet.* 2005, 37, 349). In addition, in studies of Alzheimer Disease and Parkinson's disease (cf. A. Bedalov, J. A. Simon *Science* 2004, 305, 954), resveratrol treatment prior to axotomy also decreased axonal degeneration. Resveratrol was found to protect the degeneration of neurons from axotomy in Wallerian degeneration slow mice, a genetic model of slowed axonal degeneration (NAD levels decrease in degenerating axons, and preventing this axonal NAD decline protects axons from degeneration). In PC12 cells (model system for neuronal differentiation), resveratrol-protected cells from $A\beta_{25-35}$ induced toxicity, attenuated apoptotic cell death, reduced changes in the mitochondrial membrane potential, inhibited the accumulation of intracellular reactive oxygen intermediates, and attenuated NF-κβ activation (cf. J. H. Jang, Y. J. Surh *Free Radic. Biol. Med.* 2003, 34, 1100).

In the same line, in rat hippocampal neurons, resveratrol inhibited voltage-activated $K^+$ currents, suggesting that it may be useful for treating ischemic brain injury (cf. Z. B. Gao, G. Y. Hu. *Brain Res.* 2005, 1056, 68). Resveratrol was also found to provide protection against toxicity that was induced by sodium nitroprusside (SNP) and 3-morpho-linosydnonimine (SIN-1)-induced NO in mixed hippocampal cells from Sprague-Dawley rats (cf. S. Bastianetto, W. H. Zheng, R. Quirion *Br. J. Pharmacol.* 2000, 131, 711) and against kainic acid-induced excitotoxicity in the cortex and hippocampus of Wistar rats (cf. M. Virgili, A. Contestabile *Neurosci. Lett.* 2000, 281, 123). In an anoxia-reoxygenation model for stroke using Wistar rat cerebral mitochondria, resveratrol inhibited cytochrome C release, decreased the production of superoxide anion ($O_2^-$) and $O_2$ consumption, and partly reversed the decline of the respiratory control ratio (cf. R. Zini et al. *Life Sci.* 2002, 71, 3091). After induced-stroke by the occlusion of common cortical arteries, resveratrol decreased delayed neuronal cell death and glial cell activation in Mongolian gerbils (cf. Q. Wang et al. *Brain Res.* 2002, 958, 439), prevented motor impairment, increased the levels of malodialdehyde, reduced glutathione, and decreased the volume of infarct in Wistar rats (cf. K. Sinha, G. Chaudhary, Y. K. Gupta *Life Sci.* 2002, 71, 655). Resveratrol also protected neurons, via antiplatelet aggregation, against vasodilating and antioxidant effects in Long-Evans rats (cf. S. S. Huang et al. *Life Sci.* 2001, 69, 1057). Resveratrol attenuated increased levels of malodialdehyde following kainic acid-induced seizure and epilepsy in albino Wistar rats (cf. Y. K. Gupta, S. Briyal, G. Chaudhary op. cit.).

These findings provide evidence that resveratrol and resveratrol analogues or calorie restriction mimetics can be useful in the protection from different types of neurological disorders.

Some of the properties listed above have also been observed in other trans-stilbenes of natural origin such as pterostilbene (cf. M. Tolomeo et al. *Int. J. Chem. Cell Biol.* 2005, 37, 1709), piceatannol (cf. L.-M. Hung et al. *Free Radical Biol. Med.* 2001, 30, 877; G. A. Potter et al. *Brit. J. Cancer* 2002, 86, 774) and isorhapontigenin (cf. Y. Liu, G. Liu *Biochem. Pharmacol.* 2004, 67, 777), as well as in derivatives or metabolites of resveratrol such as piceid, viniferin, resveratrol-3-sulfate, resveratrol-3-O-glucuronide and dihydro-resveratrol. In addition, several fluorinated and methoxylated analogues of these compounds have proved to be interesting candidates for the discovery of new chemopreventive and therapeutic treatments for cancer (cf. M. Roberti et al. *J. Med. Chem.* 2003, 46, 3546; S. Kim et al. *J. Med. Chem.* 2002, 45, 160).

Despite the therapeutic potential of resveratrol and other natural stilbenes, the results obtained from several pharmacokinetic studies indicate that circulating resveratrol is rapidly metabolized and has a low bioavailability (cf. J. A. Baur, D. A. Sinclair op. cit.).

Several resveratrol analogs have been described, such as 5-(6-hydroxynaphthalen-2-yl)benzene-1,3-diol (cf. F. Minutolo et al. *J. Med. Chem.* 2005, 48, 6783), (E)-2,2'-(5-(2-(pyridin-2-yl)-1,3-phenylene)bis(oxy)diacetic acid (cf. G. Chen et al. *Chem. Pharm. Bull.* 2005, 53, 1587), (E)-5-(3,5-dimethoxystyryl)-2-methoxyphenol (cf. M. Roberti et al. op. cit.), (E)-3-tert-butil-5-(3,5-dimethoxystyryl)benzene-1,2-diol (cf. R. Amorati et al. *J. Org. Chem.* 2004, 69, 7101), (E)-1,2-bis(3,5-dimethoxyphenyl)ethene (cf. S. Kim et al. op. cit.) and (Z)-5-(2-fluoro-2-(4-hydroxyphenyl)vinyl)benzene-1,3-diol (cf. S. Eddarir, Z. Abdelhadi, C. Rolando *Tetrahedron Lett.* 2001, 42, 9127). It also has been described the usefulness of nitrogenated heterocycles such as pyrroles and indoles as analogs of resveratrol (cf. F. P. Cossio et al. WO/2006/108864). Synthetic activators of Sir2 enzymes such as SRT1720 have been described as well, with therapeutic potential for treating diabetes (cf. J. C. Milne et al. *Nature* 2007, 450, 712). In general it can be said, however, that most synthetic analogues of resveratrol conserve the stilbene structure, along with the problems of bioavailability and pharmacokinetic profile associated with it.

In regard to inhibitors of sirtuins, synthetic molecules have also been described, such as splitomycin (cf. A. Bedalov et al. *Proc. Natl. Acad. Sci. USA* 2001, 98, 15113), sirtinol (cf. C. M. Grozinger et al. *J. Biol. Chem.* 2001, 276, 38837), cambinol (cf. B. Heitweg et al. *Cancer Res.* 2006, 66, 4368), dihydrocoumarin (cf. A. J. Olaharski et al. *PLoS Genet.* 2005, 1, e77), some indole derivatives (cf. A. D. Napper et al. *J. Med. Chem.* 2005, 48, 8045) or salermide (cf. E. Lara et al. *Oncogene* 2009, 28, 781). These molecules are able to inhibit sirtuins with IC50 values in the micromolar range, and have shown potent antitumor activity in vivo and in vitro, mainly by means of induction of apoptosis of tumor cells through induction of proapoptotic genes that are aberrantly repressed in cancer cells. However, the potencies of the inhibitors described to date can be improved significantly.

DESCRIPTION OF THE DRAWINGS

FIG. 1 shows how activators of the enzyme SIRT1 are measured both as the concentration of compound required to increase the enzyme activity by 50% (EC1.5) as well as by the percentage of maximum activation achieved (Max %).

SUMMARY OF THE INVENTION

A first aspect of the invention is a compound of general formula (I),

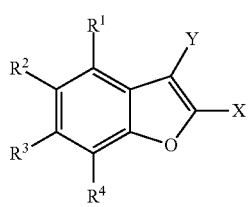

(I)

wherein:
$R^1$, $R^2$, $R^3$ and $R^4$ are, independently of each other, selected from the group consisting of alkoxy of linear or branched alkyl chain, hydrogen, halogen, nitro, cyano and hydroxyl, or wherein either pair $R^1R^2$, $R^2R^3$ or $R^3R^4$ together form a phenyl group;

one of X and Y is hydrogen, halogen or $C_1$-$C_3$alkyl; and the other one is a group of formula (V):

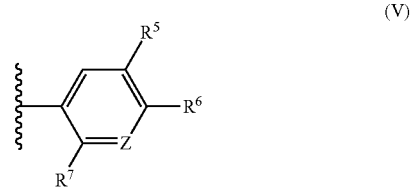

(V)

wherein:
$R^5$, $R^6$ and $R^7$ are, independently of each other, selected from the group consisting of hydrogen, halogen, hydroxy, nitro, cyano and alkoxy of linear or branched alkyl chain, Z represents a nitrogen atom or a —(C—$R^8$)— group wherein, $R^6$ is selected from the group consisting of hydrogen, hydroxyl, nitro, cyano and alkoxy of linear or branched alkyl chain;

and wherein $R^1$ and $R^3$ are hydroxyl groups when Z is —(C—$R^8$)— with the proviso that at least one of $R^1$, $R^2$, $R^3$, $R^4$, $R^5$, $R^6$, $R^7$ or $R^8$ is hydroxyl or alkoxy group of linear or branched alkyl chain;

and with the proviso that the compound of formula (I) is not 3-(4-bromo-7-methoxy-benzofuran-2-yl)-pyridine or 2-(6-methoxypyridin-3-yl)benzofuran;

or a solvate or a salt or prodrug thereof. Likewise, another aspect of the invention is the process for the preparation of a compound of general formula (I), or a solvate or a salt or prodrug thereof.

Another aspect of the present invention relates to a compound of general formula (I), or a salt, solvate or prodrug thereof, for use as medicament.

Another aspect of the present invention relates to a compound of general formula (I), or a salt, solvate or prodrug thereof, for use in the treatment of cancer, diabetes, aging related diseases or processes, or neurodegenerative diseases.

Another aspect of the present invention relates to the use of a compound of general formula (I), or a salt, solvate or prodrug thereof, in the preparation of a medicament for the treatment of cancer, diabetes, aging related diseases or processes, or neurodegenerative diseases.

According to another aspect, the present invention is directed to a method of treating cancer, diabetes, aging related diseases or processes, or neurodegenerative diseases, which comprises the administration to a patient needing such treatment, of a therapeutically effective amount of at least one compound of general formula (I) or a salt, solvate or prodrug thereof.

A further aspect of the invention is a pharmaceutical composition comprising at least one compound of general formula (I), or a pharmaceutically acceptable salt, solvate or prodrug thereof, and at least one pharmaceutically acceptable excipient.

DETAILED DESCRIPTION OF THE INVENTION

According to a particular embodiment, $R^1$ and $R^2$ or $R^3$ and $R^4$ can be bound to each other forming a α- or β-naphthyl ring (representative compounds are those of examples 6 and 7). When either pair $R^1R^2$, $R^2R^3$ or $R^3R^4$ together form a phenyl group, the resulting compound is a compound with a naphtho[2,1-b]furan, naphtho[2,3-b]furan or naphtho[1,2-b]skeleton respectively.

According to an embodiment, at least two of $R^1$, $R^2$, $R^3$, $R^4$, $R^5$, $R^6$, $R^7$ or $R^8$ are hydroxyl or alkoxy group of linear or branched alkyl chain. According to an embodiment, at least three of $R^1$, $R^2$, $R^3$, $R^4$, $R^5$, $R^6$, $R^7$ or $R^8$ are not hydrogen. According to a further embodiment, $R^1$ and $R^3$ are hydroxyl or alkoxy group of linear or branched alkyl chain.

According to a particular embodiment, Z is a nitrogen atom. According to a further embodiment, Z is a nitrogen atom and $R^6$ and $R^7$ are an alkoxy group of linear or branched alkyl chain. According to a further embodiment, each alkoxy group of linear or branched alkyl chain is independently selected from —O—$C_1$-$C_3$alkyl, preferably methoxy.

According to a particular embodiment, Z is —(C—$R^8$)— and $R^1$ and $R^3$ are hydroxyl groups. According to a further embodiment, Z is —(C—$R^8$)—, $R^1$ and $R^3$ are hydroxyl groups and $R^8$ and $R^5$ are not hydrogen. According to a further embodiment, $R^5$ and $R^8$ are both the same selected from the group consisting of —F, hydroxyl or methoxy. According to a further embodiment, Z is —(C—$R^8$)—, $R^1$ and $R^3$ are hydroxyl groups and $R^6$ is selected from the group consisting of —F, hydroxyl, —O—$C_1$-$C_3$ alkyl, nitro and cyano.

In a further aspect the invention is directed to a compound selected from the group consisting of:
2-(4-fluorophenyl)-4,6-dimethoxy-1-benzofuran
4,6-dimethoxy-2-(3,4,5-trimethoxyphenyl)-1-benzofuran
3-(4,6-dimethoxy-1-benzofuran-2-yl)-2,6-dimethoxypyridine
4,6-dimethoxy-2-(4-nitrophenyl)-1-benzofuran
4-(4,6-dimethoxy-1-benzofuran-2-yl)benzonitrile
5-bromo-4,6-dimethoxy-2-(4-methoxyphenyl)-1-benzofuran
3,5-dibromo-2-(4-fluorophenyl)-4,6-dimethoxy-1-benzofuran
2-(3,5-dihydroxyphenyl)-1-benzofuran-4,6-diol
2-(4-hydroxyphenyl)-1-benzofuran-4,6-diol
2-(4-fluorophenyl)-1-benzofuran-4,6-diol
5-(4,6-dihydroxy-1-benzofuran-2-yl)benzene-1,2,3-triol
2-(2,6-dimethoxypyridin-3-yl)benzofuran-4,6-diol
2-(3,5-difluorophenyl)benzofuran-4,6-diol
3-(3,5-difluorophenyl)-4,6-dimethoxy-1-benzofuran
3-(4-hydroxyphenyl)-1-benzofuran-4,6-diol
3-(3,5-difluorophenyl)-1-benzofuran-4,6-diol
2-bromo-4,6-dimethoxy-3-(4-methoxyphenyl)benzofuran
2-iodo-4,6-dimethoxy-3-(4-methoxyphenyl)benzofuran
3-(4-fluorophenyl)benzofuran-4,6-diol
2-bromo-3-(3,5-difluorophenyl)benzofuran-4,6-diol
or a solvate or a salt or prodrug thereof.

According to a further embodiment, Y is hydrogen and X is a group of formula (V). According to a further embodiment, X is a group of formula (V) and Y is selected from halogen, preferably bromide.

According to a further embodiment, Y is a group of formula (V) and X is a halogen, preferably bromide or iodide, or a methyl group. According to a further embodiment, Y is a group of formula (V) and X is hydrogen.

According to a further embodiment, Z is —(C—$R^8$)—, wherein $R^5$, $R^7$ and $R^8$ are hydrogen, $R^1$ and $R^3$ are hydroxyl groups and $R^6$ is selected from the group consisting of hydroxyl, halogen, preferably —F, —O—$C_1$-$C_3$alkyl, nitro, cyano.

In a preferred embodiment, the compound of general formula (I) is 2-(3,5-dihydroxyphenyl)-1-benzofuran-4,6-diol, with the following structural formula:

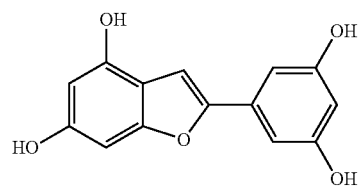

In a preferred embodiment, the compound of general formula (I) is 2-(4-hydroxyphenyl)-1-benzofuran-4,6-diol, with the following structural formula:

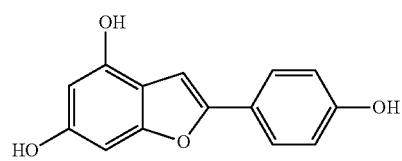

In a preferred embodiment, the compound of general formula (I) is 2-(4-fluorophenyl)-1-benzofuran-4,6-diol, with the following structural formula:

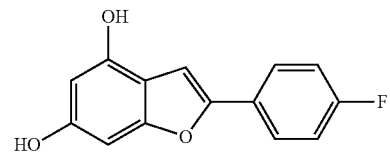

In a preferred embodiment, the compound of general formula (I) is 5-(4,6-dihydroxy-1-benzofuran-2-yl)benzene-1,2,3-triol, with the following structural formula:

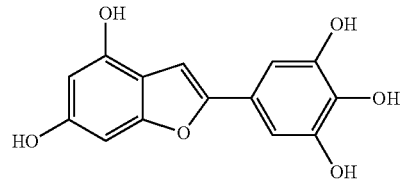

In a preferred embodiment, the compound of general formula (I) is 3-(4-hydroxyphenyl)-1-benzofuran-4,6-diol, with the following structural formula:

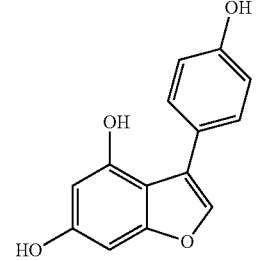

In a preferred embodiment, the compound of general formula (I) is 2-bromo-3-(3,5-difluorophenyl)-1-benzofuran-4,6-diol, with the following structural formula:

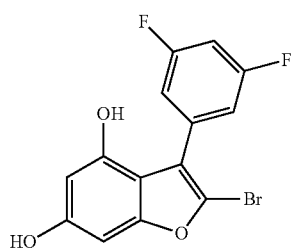

The compounds of formula (I) can be in the form of solvates or salts or prodrugs, preferably as a pharmaceutically acceptable species.

The term "alkyl" refers to a linear or branched hydrocarbon chain radical consisting of carbon and hydrogen atoms, containing no unsaturation, having the carbon atoms indicated in each case, which is attached to the rest of the molecule by a single bond. Exemplary alkyl groups can be methyl, ethyl, n-propyl, or i-propyl, "Halogen" refers to —F, —Cl, —Br or —I.

"Alkoxy" refers to a radical of the formula —O-alkyl where "alkyl" is as defined above, having between 1 and 6 carbon atoms. In an embodiment of the invention alkoxy refers to a radical of formula —O—$C_1$-$C_3$alkyl. Exemplary alkoxy radicals are methoxy, ethoxy, n-propoxy or i-propoxy.

The term "pharmaceutically acceptable species" refers to compositions and molecular entities that are physiologically tolerable and do not typically produce an allergic reaction or a similar unfavorable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly, in humans.

The term "prodrug" is used in its broadest sense and encompasses those derivatives that are converted in vivo into the compounds of the invention, such as methoxy groups or similars.

The term "solvate" means any form of the active compound of the invention which has another molecule (for example a polar solvent such as water or ethanol, a cyclodextrin or a dendrimer) attached to it through noncovalent bonds. Methods of solvation are known within the art.

The invention also provides salts of the compounds of the invention. Non-limiting examples are sulphates; hydrohalide salts; phosphates; lower alkane sulphonates; arylsulphonates; salts of $C_1$-$C_{20}$ aliphatic mono-, di- or tribasic acids which may contain one or more double bonds, an aryl nucleus or other functional groups such as hydroxy, amino, or keto; salts of aromatic acids in which the aromatic nuclei may or may not be substituted with groups such as hydroxyl, lower alkoxyl, amino, mono- or di-lower alkylamino sulphonamido. Also included within the scope of the invention are quaternary salts of the tertiary nitrogen atom with lower alkyl halides or sulphates, and oxygenated derivatives of the tertiary nitrogen atom, such as the N-oxides. In preparing dosage formulations, those skilled in the art will select the pharmaceutically acceptable salts.

Solvates, salts and prodrugs can be prepared by methods known in the state of the art. Note that the non-pharmaceutically acceptable solvates and prodrugs also fall within the scope of the invention because they can be useful in preparing pharmaceutically acceptable salts, solvates or prodrugs.

The compounds of the invention also seek to include compounds that differ only in the presence of one or more isotopically enriched atoms. For example, compounds having the present structures except for the replacement of a hydrogen by a deuterium or tritium, or the replacement of a carbon by a carbon enriched in $^{11}C$, $^{13}C$ or $^{14}C$ or a $^{15}N$ enriched nitrogen are within the scope of this invention.

Synthesis of Compounds of Formula (I)

Multiple methods have been described for the synthesis of benzofurans (cf. A. R. Katritzky, C. W. Rees, E. F. V. Scriven, Eds.: Comprehensive Heterocyclic Chemistry II; Pergamon Press, Oxford, 1996, Vol. 2, pp 259-287; X.-L. Hou et al. *Prog. Heterocycl. Chem.* 2008, 19, 176; M. G. Kadieva, E. T. Oganesyan *Chem. Heterocycl. Compd.* 1997, 33, 1245; L. de Luca et al. *Curr. Med. Chem.* 2009, 16, 1). For example, by formation of 2-substituted and 2,3-disubstituted benzofurans by means of the reaction between phenols and vinyl sulfoxides (cf. J. B. Hendrickson, M. A. Walker *Org. Lett.* 2000, 2, 2729), between protected phenols and Schrock nickel-carbenes (cf. G. J. McKiernan, R. C. Hartley *Org. Lett.* 2003, 5, 4389), α-alkynylphenols in the presence of various metals (cf. M. Nakamura et al. *Org. Lett.* 2006, 8, 2803; V. Fiandanese et al. *Tetrahedron* 2008, 64, 53), with α-vinylphenols and terminal alkynes (cf. M. Nagamochi, Y.-Q. Fang, M. Lautens *Org. Lett.* 2007, 9, 2955), or with α-bromophenols and carbonyl compounds (cf. C. Eidamshaus, J. D. Burch *Org. Lett.* 2008, 10, 4211). It also has been described the formation of 2-acyl benzofurans by reaction between salicylaldehydes and α-bromoketones (cf. M. L. N. Rao, D. K. Awasthi, D. Banerjee *Tetrahedron Lett.* 2007, 48, 431).

Likewise, it has been described the synthesis of 2-substituted and 3-substituted benzofurans by intramolecular reaction of orto-substituted benzaldehydes (cf. G. A. Kraus et al. *Org. Lett.* 2000, 2, 2409), by intramolecular Heck reactions in ionic liquids (cf. X. Xie et al. *Tetrahedron Lett.* 2004, 45, 6235), by cyclization of 1-aryl-2-phenoxyethanones in the presence of boron trichloride (cf. I. Kim, S.-H. Lee, S. Lee *Tetrahedron Lett.* 2008, 49, 6579) or bismuth triflate (cf. I. Kim, J. Choi *Org. Biomol. Chem.* 2009, 7, 2788), or by a platinum-catalyzed domino dienone-phenol rearrangement/intramolecular cyclization of alkyne-containing quinols (cf. I. Kim, K. Kim, J. Choi *J. Org. Chem.* 2009, 74, 8492).

Another aspect of the invention refers to procedures to obtain compounds of general formula (I). The following methods A and B describe the procedures for obtaining compounds of general formula (I), or solvates or salts or prodrugs thereof, among which include compounds of formula (Ia) and (Ib).

Method A

Wang, Z. *Synthetic Communications,* 2009, 39, 4079-4087, describes the synthesis of 3-substituted benzofurans by reaction of the corresponding phenacyl bromide and phenol in the presence of an inorganic base and microwave radiation. The compounds synthesized include 6-Methoxy-3-phenyl-benzofuran and 4-Methoxy-3-phenyl-benzofuran. In this paper mixtures of the Williamson product (namely, the β-oxoether) and its cycloadduct (i.e. the 3-substituted benzo[b]furan) are obtained. No 2-substituted derivatives were observed under the reaction conditions described in this article.

However, the inventors have found that the reaction in the absence of a base surprisingly provides the 2-substituted derivatives in very high yield, and very low amounts of byproducts. Accordingly, a further aspect of the invention is a method, Method A, for the preparation of compounds of general formula (Ia):

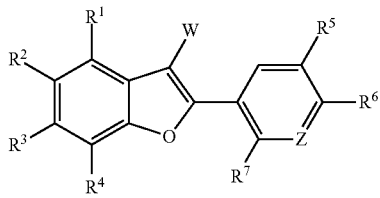

(Ia)

wherein $R^1$, $R^2$, $R^3$, $R^4$, $R^5$, $R^6$, $R^7$ and Z have the meaning given above, and W can be a hydrogen atom or a halogen atom or a $C_1$-$C_3$alkyl group, which comprises reacting:

a) a compound of general formula (IIa),

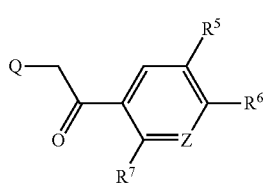

(IIa)

wherein Q can be a chlorine, bromine or iodine atom, or a leaving group such as mesylate or tosylate, and $R^5$, $R^6$, $R^7$ have the meaning given above, except for hydroxyl group, and Z has the meaning given above, except for —(C—OH)—; with b) a compound of general formula (III),

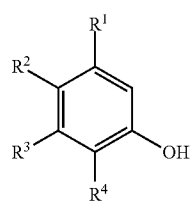

(III)

wherein $R^1$, $R^2$, $R^3$ and $R^4$ have the meaning given above, except for hydroxyl group;
in the presence of
c) neutral alumina ($Al_2O_3$); and
d) a solvent, preferably a nonpolar solvent such as a linear or branched aliphatic hydrocarbon of $C_5$-$C_{10}$ carbons or an aromatic hydrocarbon such as toluene, xylene or similar.
and in the absence of bases, such as carbonates of alkaline metals or alkaline earth metals (e.g. sodium, lithium, potassium, calcium, or magnesium carbonate), sulfates of alkaline metals or alkaline earth metals (e.g. sodium, lithium, potassium, calcium, or magnesium sulfate), acetates of alkaline metals or alkaline earth metals (e.g. sodium, lithium, potassium, calcium, or magnesium acetate), hydroxides of alkaline metals or alkaline earth metals (e.g. sodium, lithium, potassium, calcium, or magnesium hydroxide) or phosphates, monohydrogen phosphates or dihydrogen phosphates of alkaline metals or alkaline earth metals (e.g. sodium, lithium, potassium, calcium, or magnesium phosphate, or potassium dihydrogen phosphate). That is, the initial mixture of materials a), b), c) and d) does not include a base. The reaction usually takes place at temperatures ranging from 0° C. to +160° C. until completion of the reaction.

For the aims of the invention, the reaction mixture made up of the four compounds of phases a) to d) can be made by adding one of the components to the mixture formed by the three other components at a temperature ranging from +25° C. to +160° C. After completion of the addition, the resulting mixture is stirred until completion of the reaction.

To obtain the compounds of formula (Ia) containing hydroxyl groups, the corresponding alkoxy, e.g. methoxy, cycloadducts obtained following the procedure described above can be deprotected by known procedures, for example, by treatment with boron tribromide (see for example *Tetrahedron* 1968, 24(5), 2289-2292). In an embodiment of the invention the reaction takes place in a halogenated solvent under dry atmosphere at a temperature ranging from 0° C. to +40° C. The mono- or polyhydroxylated products thus obtained can be isolated and purified by following known techniques.

In an embodiment of the invention compounds of formula (Ia) containing halogen atoms other than fluorine, can be obtained by halogenation. For example, the cycloadducts obtained can be treated with N-halosuccinimide (where "halo" denotes chlorine, bromine or iodine) in an appropriate solvent at a temperature ranging from 0° C. to +40° C. until completion of the reaction. The mono- or polyhalogenated products thus obtained (depending on the number of equivalents of N-halosuccinimide used) can be isolated and purified by following known techniques.

Method B

Method B represents a procedure for the preparation of compounds of general formula (Ib):

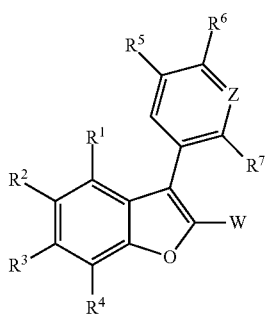

(Ib)

wherein $R^1$, $R^2$, $R^3$, $R^4$, $R^5$, $R^6$, $R^7$, Z and W have the meaning given in the description of Method A, which comprises reacting:

a) a compound of general formula (IIb),

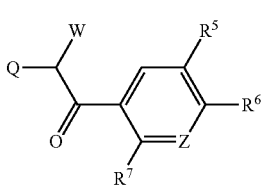

(IIb)

where $R^5$, $R^6$, $R^7$, W and Q have the meaning given in the description of Method A;

with
b) a compound of general formula (III),

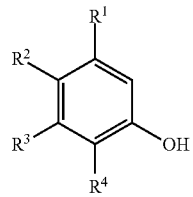

where $R^1$, $R^2$, $R^3$ and $R^4$ have the meaning given in the description of Method A;
in the presence of
c) a suspension of a base, such as potassium carbonate, in an appropriate solvent such as acetone or other liquid ketone at room temperature.

Alternative bases c) may be selected from the group consisting of carbonates of alkaline metals or alkaline earth metals (e.g. sodium, lithium, calcium, or magnesium carbonate), sulfates of alkaline metals or alkaline earth metals (e.g. sodium, lithium, potassium, calcium, or magnesium sulfate), acetates of alkaline metals or alkaline earth metals (e.g. sodium, lithium, potassium, calcium, or magnesium acetate), hydroxides of alkaline metals or alkaline earth metals (e.g. sodium, lithium, potassium, calcium, or magnesium hydroxide) or phosphates, monohydrogen phosphates or dihydrogen phosphates of alkaline metals or alkaline earth metals (e.g. sodium, lithium, potassium, calcium, or magnesium phosphate, or potassium dihydrogen phosphate).

The reaction usually takes place at temperatures ranging from +100° C. to +150° C., either by thermal heating or under microwave irradiation until completion of the reaction to obtain ethers of general formula (IV):

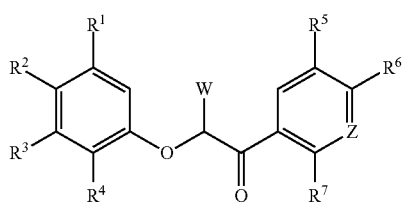

wherein W has the meaning given for compounds of general formula (IIb).

For the aims of the invention, the reaction mixture made up of the compounds a) to c) can be made by adding one of the components to the mixture formed by the other components at a temperature ranging from +25° C. to +150° C., and optionally rising the temperature of the reaction mixture after completion of the addition to a temperature ranging from +100° C. to +150° C. This heating can be obtained by thermal heating or by microwave irradiation, for the time necessary to complete the reaction of formation of ethers of general formula (IV).

Once these compounds are obtained, they are dispersed in neutral alumina suspended in an appropriate aliphatic or aromatic hydrocarbon, preferably a mixture of xylenes, or in the absence of solvent, and heated to a temperature ranging from of +100° C. to +150° C. for the time needed to complete the cyclization reaction.

To obtain compounds of formula (Ib) containing hydroxyl groups, the cycloadducts obtained according to the above statement that contain alkoxy groups, e.g. methoxy groups, can be treated with boron tribromide (see for example *Tetrahedron* 1968, 24(5), 2289-2292). In an embodiment of the invention the reaction takes place in a halogenated solvent under dry atmosphere at a temperature ranging from 0° C. to +40° C. The mono- or polyhydroxylated products thus obtained can be isolated and purified by following known techniques.

In an embodiment of the invention the compounds of formula (Ib) containing halogen atoms other than fluorine can be obtained by halogenation. For example, the cycloadducts obtained can be treated with N-halosuccinimide (where "halo" denotes chlorine, bromine or iodine) in an appropriate solvent at a temperature ranging from 0° C. to +40° C. until completion of the reaction. The mono- or polyhalogenated products thus obtained (depending on the number of equivalents of N-halosuccinimide used) can be isolated and purified by following known techniques.

Compounds of formula (Ia) or (Ib) wherein W is a $C_1$-$C_3$ alkyl group may be obtained in an embodiment of the invention by alkylating the corresponding halogenated compound by known procedures such as the Suzuki, Negishi or Heck reaction. For example, 4,6-dimethoxy-2-methyl-3-phenyl-1-benzofuran may be obtained from 4,6-dimethoxy-2-bromo-3-phenyl-1-benzofuran by any of said reactions. Examples of such transformations may be found in the *J. Org. Chem.*, 2008, 73, 1131-1134 or *Tetrahedron Lett.*, 2002, 43, 9125-9127.

Microwaves may be generated using known equipment such as CEM Discover microwave reactor or a Biotage Initiator microwave reactor. More are available in the market and the skilled person may choose the most appropriate.

In an embodiment of the invention the reaction takes place by irradiating the mixture with microwaves at a power comprised between 50 W and 1200 W, preferably between 100 W and 400 W, preferably at 100 W. The pressure is typically comprised between 10 and 500 PSI, preferably between 30 and 200, more preferably between 60 and 100 PSI.

A further embodiment of the invention is a compound of formula (Ia) or a salt or solvate or prodrug thereof. A further embodiment of the invention is a compound of formula (Ib) or a salt or solvate or prodrug thereof.

The initial compounds and starting materials, e.g. the compounds of formula (IIa), (IIb) or (III), are either commercially available or can be obtained following procedures described in the literature. For example, see Chen L., Ding Q., Gillespie P., Kim K., Lovey A. J., McComas W. W., Mullin J. G. and Perrota A., (2002) PCT No. WO 2002057261 (e.g. Examples 7-13, pages 46-50; or Examples 14H-14O, pages 57-60); King L. C., Ostrum G. K. *J. Org. Chem.* 1964, 29, 3459-3461; Diwu Z., Beachdel C., Klaubert D. H. *Tetrahedron Lett.* 1998, 39, 4987-4990; Bakke B. A., McIntosh M. C., Turnbull K. D. *J. Org. Chem.* 2005, 70(1), 4338-4345).

Use of the Compounds of the Invention

According to a particular embodiment, the compounds of general formula (I) are useful for the treatment of various types of cancer, diabetes, aging related diseases or processes, or neurodegenerative diseases, by restricting tumor growth and metastasis or by activating mechanisms of apoptosis induction or other processes that stop the development of primary or metastatic tumors.

Therefore, in another aspect the invention is directed to a compound of formula (I)

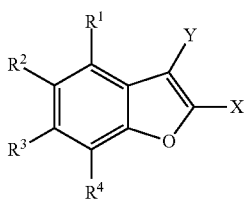

(I)

wherein:
R¹ and R³ are, independently of each other, selected from the group consisting of hydroxyl, alkoxy of linear or branched alkyl chain, hydrogen, halogen, nitro and cyano.
R² and R⁴ are, independently of each other, selected from the group consisting of alkoxy of linear or branched alkyl chain, hydrogen, halogen, nitro, cyano and hydroxyl, or wherein either pair R¹R², R²R³ or R³R⁴ together form a phenyl group;
one of X and Y is hydrogen, $C_1$-$C_3$ alkyl, or halogen; and the other one is a group of formula (V):

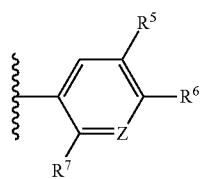

(V)

wherein:
R⁵, R⁶ and R⁷ are, independently of each other, selected from the group consisting of hydrogen, halogen, hydroxy, nitro, cyano and alkoxy of linear or branched alkyl chain,
Z represents a nitrogen atom or a —(C—R⁸)— group wherein, R⁸ is selected from the group consisting of hydrogen, hydroxyl, nitro, cyano and alkoxy of linear or branched alkyl chain;
and wherein R¹ and R³ are hydroxyl or alkoxyl groups when Z is —(C—R⁸)— with the proviso that at least one of R¹, R², R³, R⁴, R⁵, R⁶, R⁷ or R⁸ is hydroxyl or alkoxy group of linear or branched alkyl chain;
or a pharmaceutically acceptable solvate or a salt or prodrug thereof, for the use as a medicament.

In a particular embodiment, the invention is directed to a compound of formula (I) as defined in above, or a pharmaceutically acceptable solvate or a salt or prodrug thereof, for the use in the treatment of a disease or condition selected from the group consisting of cancer, diabetes, age-related diseases or processes, or neurodegenerative diseases.

According to an embodiment of the invention the neurodegenerative disease is Alzheimer or Huntington's disease.

In a particular embodiment, R¹ and R³ are hydroxyl or methoxy groups.

Further preferred embodiments of compounds of formula (I) for use as a medicament are as defined previously herein.

Pharmaceutical Compositions

The compounds of the present invention can be used with at least another drug to provide a combination therapy. This other drug or drugs may be part of the same composition, or may be provided as a separate composition and can be administered at the same time or at different times.

The term "treatment" or "treating" in the context of this document means administration of a compound or a formulation according to this invention to prevent, improve or eliminate the disease or one or more symptoms associated with the disease. "Treatment" also encompasses preventing, improving or eliminating the physiological sequalae of the disease.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21$^{st}$ Edition, 2005; or "Handbook of Pharmaceutical Excipients", Rowe C. R.; Paul J. S.; Marian E. Q., sixth Edition.

Examples of pharmaceutical compositions include any solid composition (tablets, pills, capsules, granules, etc.) or liquid composition (solutions, suspensions or emulsions) for oral, topical or parenteral administration.

In a preferred embodiment the pharmaceutical compositions are in oral delivery form. Pharmaceutical forms suitable for oral administration may be tablets and capsules and may contain conventional excipients known in the art such as binders, for example syrup, gum arabic, gelatin, sorbitol, tragacanth or polyvinylpyrrolidone; fillers, for example lactose, sugar, cornstarch, calcium phosphate, sorbitol or glycine; lubricants for the preparation of tablets, for example magnesium stearate; disintegrants, for example starch, polyvinylpyrrolidone, sodium starch glycolate or microcrystalline cellulose; or pharmaceutically acceptable wetting agents such as sodium lauryl sulphate.

Solid oral compositions can be prepared by conventional methods of blending, filling or preparation of tablets. Repeated blending operations can be used to distribute the active ingredient in all the compositions that use large amounts of fillers. Such operations are conventional in the art. The tablets can be prepared, for example, by dry or wet granulation and optionally can be coated by well known methods in normal pharmaceutical practice, in particular using a enteric coating.

Pharmaceutical compositions can also be adapted for parenteral administration, such as sterile solutions, suspensions or lyophilized products in the appropriate unit dosage form. Suitable excipients such as fillers, buffering agents or surfactants can be used.

The mentioned formulations will be prepared using standard methods such as those described or referred to in the Spanish and U.S. Pharmacopoeias and similar reference texts.

In general, the effective amount of a compound of the invention to be administered will depend on the relative efficacy of the compound chosen, the severity of the disorder being treated and the patient's weight. However, the active compounds will normally be administered one or more times a day, for example 1, 2, 3 or 4 times daily, with typical total daily doses in the range from 0.01 up to 1000 mg/kg/day.

In order to facilitate the understanding of the preceding ideas, some examples of experimental procedures and embodiments of the present invention are described below. These examples are merely illustrative.

EXAMPLES

General Synthesis Methods

Experimental Procedures of Method A

A.1) Synthesis of 2-Substituted benzo[b]furans Under Microwave Irradiation

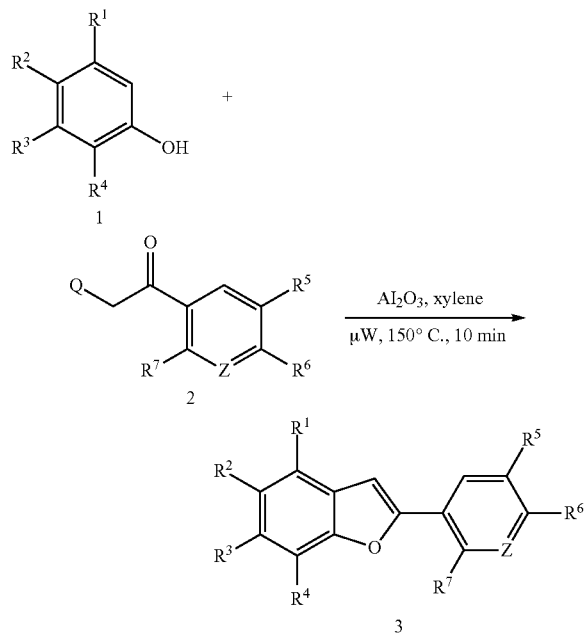

A mixture of the phenol 1 (0.5 mmol), the α-haloketone 2 (0.7 mmol) and neutral aluminium oxide (2.45 mmol, 0.25 g) in xylene (1.5 ml) was irradiated with microwaves at 150° C. and 100 W for 10 min (pressure 60-100 PSI) in a focused CEM Discover microwave reactor. The resulting mixture was filtered through a Celite pad and evaporated. The residue was purified by column chromatography on silicagel using ethyl acetate:hexane as eluent to yield the corresponding product 3.

A.2) Synthesis of 2-substituted benzo[b]furans Under Classical Heating

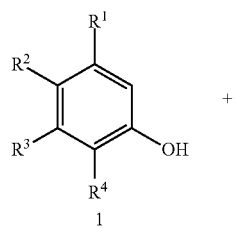

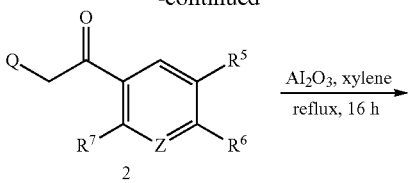

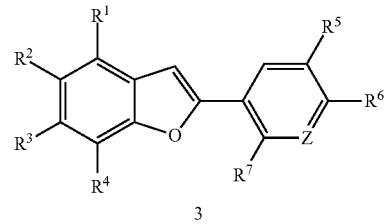

A mixture of the phenol 1 (3.0 mmol), the α-haloketone 2 (4.2 mmol) and neutral aluminium oxide (21 mmol, 2.14 g) was refluxed in xylene (12 ml) at 145° C. for 16 hours. The resulting mixture was filtered through a Celite pad and evaporated. The residue was purified by column chromatography on silicagel using ethyl acetate:hexane as eluent to yield the corresponding product 3.

A.3) Monohaloaenation of 2-substituted benzo[b]furans

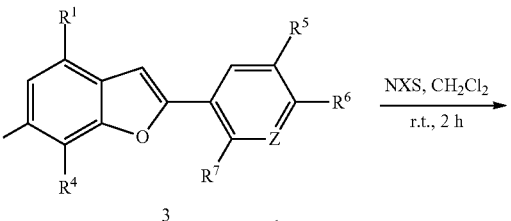

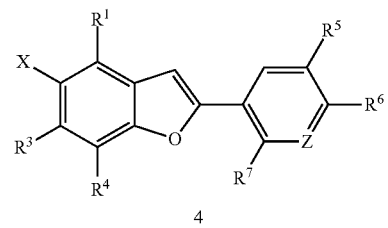

A solution of the benzofuran 3 (1.27 mmol) in dichloromethane (18 ml) was added dropwise to a solution of N-halosuccinimide (1.20 mmol) in dicholoromethane (18 ml). The mixture was stirred at room temperature for 2 hours and then evaporated. The residue was purified by column chromatography on silicagel using ethyl acetate:hexane 1:10 as eluent to yield the corresponding product 4.

A.4) Dihalogenation of 2-substituted benzo[b]furans

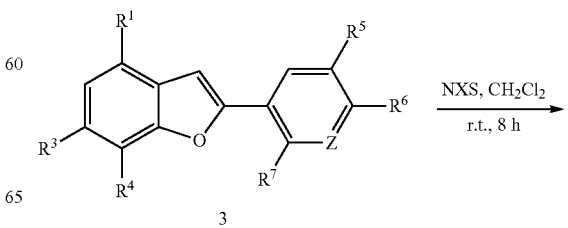

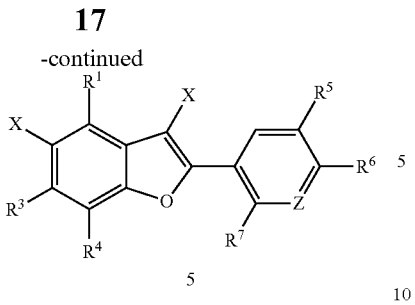

5

A solution of the benzofuran 3 (0.528 mmol) in dichloromethane (5 ml) was added dropwise to a solution of N-halosuccinimide (1.056 mmol) in dichloromethane (5 ml). The mixture was stirred at room temperature for 8 hours and then evaporated. The residue was purified by column chromatography on silicagel using ethyl acetate:hexane 1:10 as eluent to yield the corresponding product 5.

A.5) Deprotection of Methoxy Groups

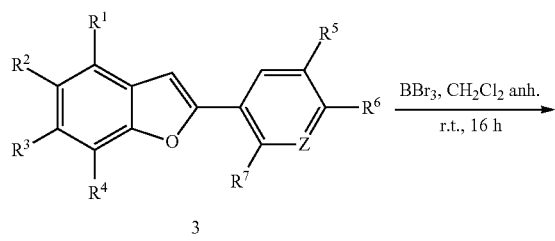

3
any $R^1$, $R^2$, $R^3$, $R^4$, $R^5$, $R^6$ and/or $R^7$ = $OCH_3$

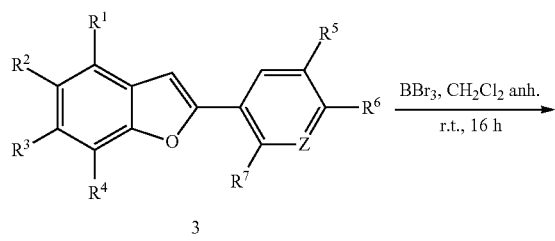

6
any $R^1$, $R^2$, $R^3$, $R^4$, $R^5$, $R^6$ and/or $R^7$ = OH

Boron tribromide (1M in dichloromethane, 2 equivalents per methoxy group to be deprotected) was added dropwise to a solution of the corresponding benzofuran 3 (0.3 mmol) in anhydrous dichloromethane (10 ml) at 0° C. under argon atmosphere. The mixture was stirred for 16 hours at room temperature and then methanol (approximately 1 ml per ml of boron tribromide solution used) was added dropwise at 0° C. The resulting mixture was purified by column cromatography on silicagel using ethyl acetate:hexane 1:1 as eluent to yield the corresponding product 6.

Experimental Procedures of Method B

B.1) Synthesis of α-phenoxyketones under Microwave Irradiation

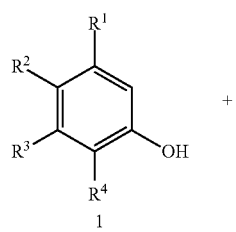

1

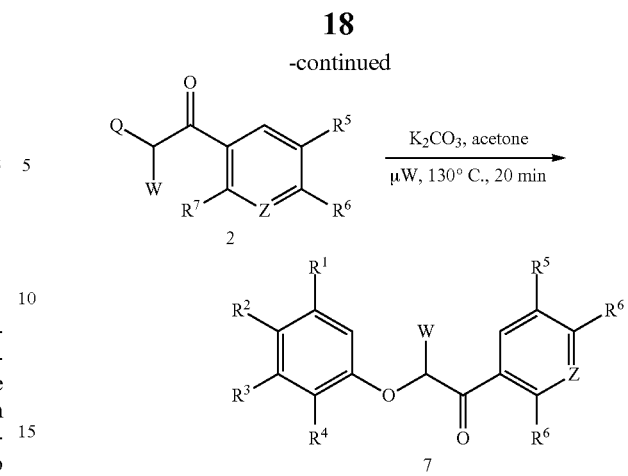

7

A mixture of the phenol 1 (2 mmol), the α-haloketone 2 (2 mmol) and potassium carbonate (4 mmol, 0.55 g) in acetone (2 ml) was irradiated with microwaves at 130° C. and 100-400 W for 10 min (pressure 5-10 bar) in a focused Biotage Initiator microwave reactor. The resulting mixture was filtered through a Celite pad and evaporated. The residue was purified by precipitation in diethylether or by column chromatography on silicagel using ethyl acetate:hexane as eluent to yield the corresponding product 7.

B.2) Synthesis of α-phenoxyketones under Classical Heating

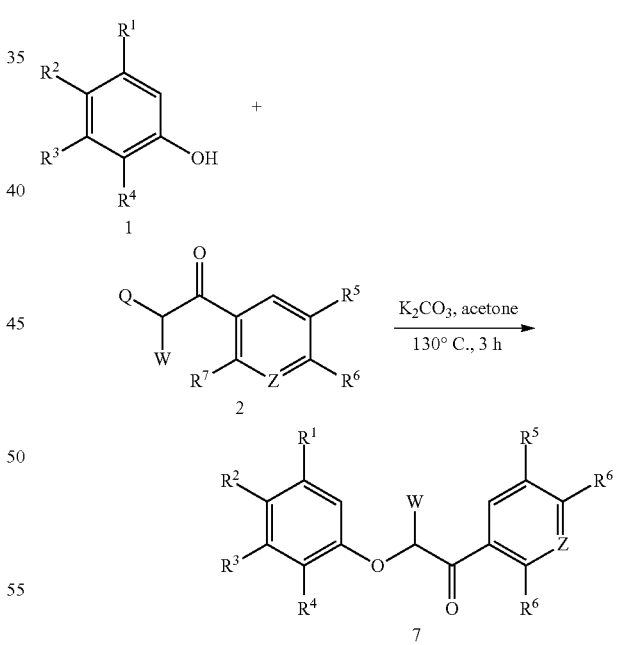

7

A mixture of the phenol 1 (7.80 mmol), the α-haloketone 2 (7.8 mmol) and potassium carbonate (15.6 mmol, 2.16 g) in acetone (6 ml) was heated in an oil bath at 130° C. (internal temperature monitored by a fibre-optic probe) for 3 hours. The resulting mixture was filtered and evaporated. The residue was purified by precipitation in diethylether or by column chromatography on silicagel using ethyl acetate:hexane as eluent to yield the corresponding product 7.

B.3) Cyclization of α-phenoxyketones: Synthesis of 3-substituted benzo[b]furans

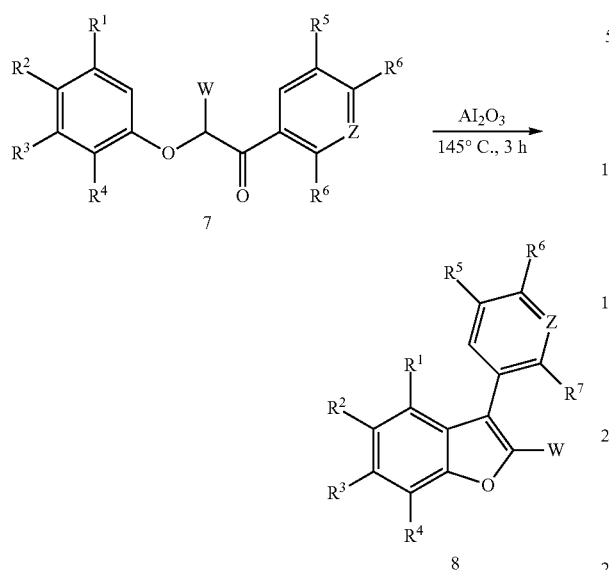

A mixture of the α-phenoxyketones 7 (2.0 mmol) and neutral aluminium oxide (34 mmol, 3.47 g) was heated in an oil bath at 145° C. (internal temperature monitored by a fibre-optic probe) for 3 hours. The resulting mixture was filtered through a Celite pad and evaporated. The residue was purified by column chromatography on silicagel using ethyl acetate:hexane as eluent to yield the corresponding product 8.

B.4) Halogenation of 3-substituted benzo[b]furans

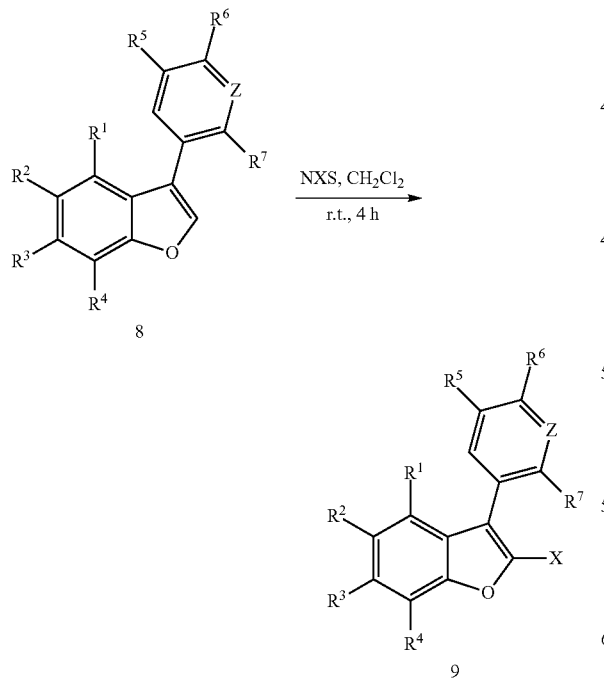

A solution of the benzofuran 8 (0.175 mmol) in dichloromethane (2.45 ml) was added dropwise to a solution of N-halosuccinimide (0.170 mmol) in dicholoromethane (2.45 ml). The mixture was stirred at room temperature for 4 hours and then evaporated. The residue was purified by column chromatography on silicagel using ethyl acetate:hexane 1:5 as eluent to yield the corresponding product 9.

B.5) Experimental Procedure of Deprotection of Methoxy Group

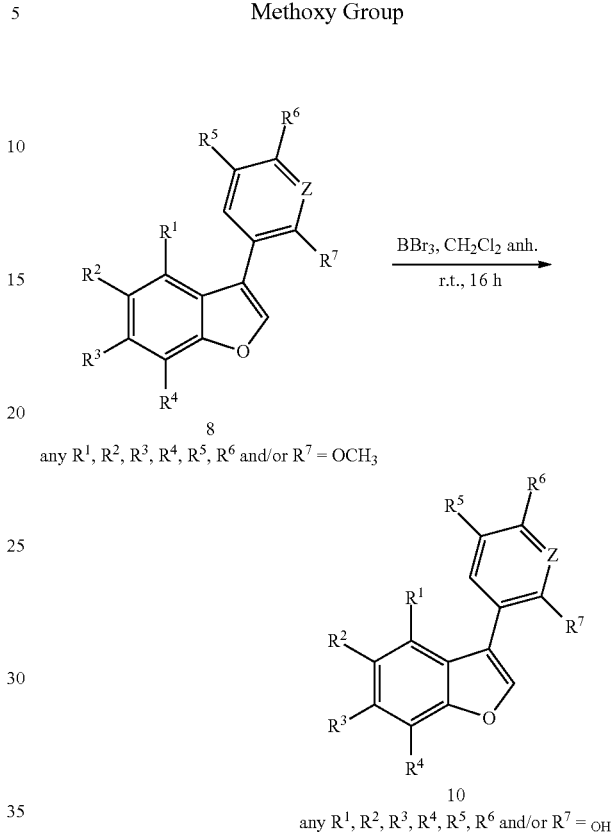

Boron tribromide (1M in dichloromethane, 2 equivalents per methoxy group to be deprotected) was added dropwise to a solution of the corresponding benzofuran 8 (0.3 mmol) in anhydrous dichloromethane (10 ml) at 0° C. under argon atmosphere. The mixture was stirred for 16 hours at room temperature and then methanol (approximately 1 ml per ml of boron tribromide solution used) was added dropwise at 0° C. The resulting mixture was purified by column cromatography on silicagel using ethyl acetate:hexane 1:1 as eluent to yield the corresponding product 10.

Synthesis of Compounds of the Invention

Example 1

Preparation of 2-(4-fluorophenyl)-4,6-dimethoxy-1-benzofuran, with the Following Structural Formula

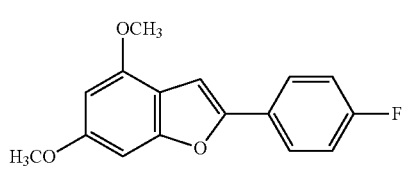

This compound was prepared using Method A from 3,5-dimethoxyphenol and 2-bromo-1-(4-fluorophenyl)ethanone:

Yield 49% following procedure A.2; m.p. 142-143° C.; IR 2914, 1614, 1496, 1220, 1145, 1116, 1043 cm$^{-1}$; $^{1}$H-NMR (200 MHz, δ ppm, CDCl$_3$) 7.74 (dd, J=8.8 Hz, 5.4 Hz, 2H), 7.10 (t, J=8.7 Hz, 2H), 6.96 (s, 1H), 6.68 (s, 1H), 6.33 (d, J=1.7 Hz, 1H), 3.89 (d, J=11.3 Hz, 6H); $^{13}$C-NMR (126 MHz, δ ppm, CDCl$_3$) 162.6 (d, J=247.7 Hz), 159.5, 156.8, 153.7, 153.0, 127.4 (d, J=3.0 Hz), 126.2 (d, J=8.0 Hz), 115.9 (d, J=22.0 Hz), 113.5, 98.7, 94.6, 88.5, 55.9, 55.8.

Example 2

Preparation of 4,6-dimethoxy-2-(3,4,5-trimethoxyphenyl)-1-benzofuran, with the Following Structural Formula

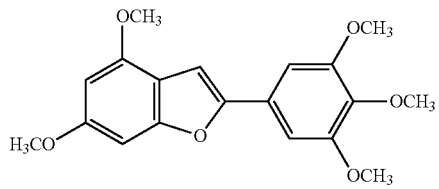 [SMILES: COc1cc(OC)c2cc(-c3cc(OC)c(OC)c(OC)c3)oc2c1]

This compound was prepared using Method A from 3,5-dimethoxyphenol and 2-bromo-1-(3,4,5-trimethoxyphenyl)ethanone: Yield 75% following procedure A.2; m.p. 131-132° C.; IR 2960, 1619, 1497, 1227, 1203, 1134, 1110 cm$^{-1}$; $^{1}$H-NMR (500 MHz, δ ppm, CDCl$_3$) 7.04 (s, 2H), 7.00 (s, 1H), 6.74 (s, 1H), 6.36 (d, J=1.8 Hz, 1H), 3.97 (s, 6H), 3.95 (s, 3H), 3.91 (s, 3H), 3.89 (s, 3H); $^{13}$C-NMR (126 MHz, δ ppm, CDCl$_3$) 159.4, 156.7, 153.8, 153.7, 153.6, 138.4, 126.6, 113.5, 101.9, 98.7, 94.6, 88.5, 61.2, 56.4, 56.0, 55.8.

Example 3

Preparation of 3-(4,6-dimethoxy-1-benzofuran-2-yl)-2,6-dimethoxypyridine, with the Following Structural Formula

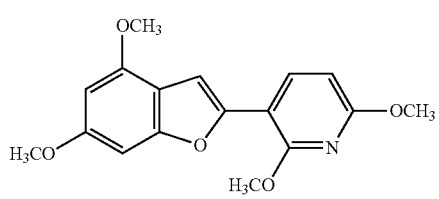

This compound was prepared using Method A from 3,5-dimethoxyphenol and 2-bromo-1-(2,6-dimethoxypyridin-3-yl)ethanone: Yield 53% following procedure A.2; m.p. 155-156° C.; IR 2937, 2961, 1605, 1504, 1475, 1460, 1272, 1107, 1011 cm$^{-1}$; $^{1}$H-NMR (500 MHz, δ ppm, CDCl$_3$) 8.12 (d, J=8.2 Hz, 1H), 7.18 (s, 1H), 6.66 (s, 1H), 6.41 (d, J=8.2 Hz, 1H), 6.32 (s, 1H), 4.10 (s, 3H), 3.96 (s, 3H), 3.93 (s, 3H), 3.85 (s, 3H); $^{13}$C-NMR (126 MHz, δ ppm, CDCl$_3$) 161.9, 159.1, 158.7, 155.9, 153.7, 149.7, 137.4, 113.9, 106.7, 101.7, 101.5, 94.3, 88.4, 55.9, 55.8, 53.8, 53.7.

Example 4

Preparation of 4,6-dimethoxy-2-(4-nitrophenyl)-1-benzofuran, with the Following Structural Formula

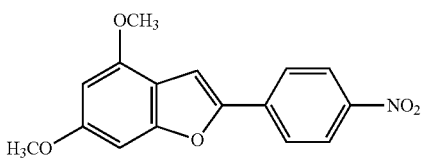 [SMILES: COc1cc(OC)c2cc(-c3ccc([N+](=O)[O-])cc3)oc2c1]

This compound was prepared using Method A from 3,5-dimethoxyphenol and 2-bromo-1-(4-nitrophenyl)ethanone: Yield 44% following procedure A.2; m.p. 192-193° C.; IR 2943, 2914, 1594, 1504, 1319, 1145, 1104 cm$^{-1}$; $^{1}$H-NMR (500 MHz, δ ppm, CDCl$_3$) 8.26 (d, J=8.8 Hz, 2H), 7.88 (d, J=8.8 Hz, 2H), 7.24 (s, 1H), 6.69 (s, 1H), 6.34 (s, 1H), 3.93 (s, 3H), 3.88 (s, 3H); $^{13}$C-NMR (75 MHz, δ ppm, DMSO-d$_6$) 160.3, 156.7, 153.6, 150.6, 146.1, 135.9, 124.5, 124.3, 112.4, 103.9, 94.9, 88.5, 55.8, 55.7.

Example 5

Preparation of 4-(4,6-dimethoxy-1-benzofuran-2-yl)benzonitrile, with the Following Structural Formula

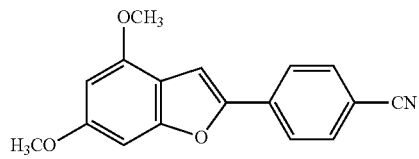

This compound was prepared using Method A from 3,5-dimethoxyphenol and 4-(2-bromoacetyl)benzonitrile: Yield 24% following procedure A.2; m.p. 220-221° C.; IR 3042, 2955, 2223, 1600, 1507, 1217, 1145, 1104 cm$^{-1}$; $^{1}$H-NMR (500 MHz, δ ppm, CDCl$_3$) 7.84 (d, J=8.2 Hz, 2H), 7.67 (d, J=8.3 Hz, 2H), 7.18 (s, 1H), 6.68 (s, 1H), 6.34 (s, 1H), 3.92 (s, 3H), 3.87 (s, 3H); $^{13}$C-NMR (126 MHz, δ ppm, CDCl$_3$) 160.5, 157.4, 154.2, 151.6, 134.9, 132.8, 124.5, 119.1, 113.4, 110.8, 102.4, 94.9, 88.4, 56.1, 55.9.

Example 6

Preparation of 5-bromo-4,6-dimethoxy-2-(4-methoxyphenyl)-1-benzofuran, with the Following Structural Formula

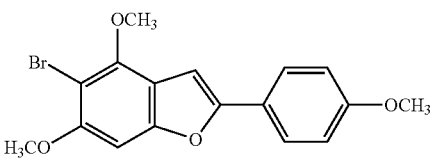 [SMILES: COc1ccc(-c2cc3c(OC)c(Br)c(OC)cc3o2)cc1]

This compound was prepared using Method A from 3,5-dimethoxyphenol and 2-bromo-1-(4-methoxyphenyl)ethanone: Yield 81% following procedures A.2 and A.3; m.p. 107-109° C.; IR 2949, 2827, 1600, 1508, 1252, 1214, 1125, 1040 cm$^{-1}$; $^{1}$H-NMR (200 MHz, δ ppm, CDCl$_3$) 7.77 (d, J=8.7 Hz, 2H), 6.97 (d, J=8.7 Hz, 2H), 6.95 (s, 1H), 6.41 (s, 1H), 3.97 (s, 6H), 3.86 (s, 3H); $^{13}$C-NMR (75 MHz, δ ppm, CDCl$_3$) 163.7, 160.5, 157.2, 156.4, 150.9, 126.0, 125.8, 125.7, 115.8, 115.5, 98.8, 98.4, 92.3, 90.2, 57.4, 55.9, 55.3.

Example 7

Preparation of 3,5-dibromo-2-(4-fluorophenyl)-4,6-dimethoxy-1-benzofuran, with the Following Structural Formula

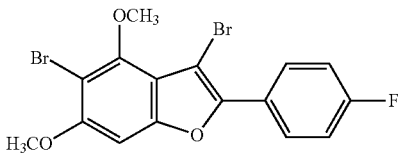 [SMILES: COc1cc2oc(-c3ccc(F)cc3)c(Br)c2c(OC)c1Br]

This compound was prepared using Method A from 3,5-dimethoxyphenol and 2-bromo-1-(4-fluorophenyl)ethanone: Yield 66% following procedures A.2 and A.4; m.p. 186-187° C.; IR 2295, 2839, 1617, 1504, 1360, 1209, 1130, 1162, 1101 cm$^{-1}$, $^1$H-NMR (500 MHz, δ ppm, CDCl$_3$) 8.13 (dd, J=8.7 Hz, 5.4 Hz, 2H), 7.16 (t, J=8.7 Hz, 2H), 6.42 (s, 1H), 3.97 (s, 3H), 3.96 (s, 3H); $^{13}$C-NMR (75 MHz, δ ppm, CDCl$_3$) 163.04 (d, J=249.8 Hz) 155.6, 153.7, 152.4, 148.8, 128.9 (d, J=8.2 Hz), 125.9 (d, J=3.2 Hz), 115.8 (d, J=21.8 Hz), 113.1, 92.9, 91.2, 85.3, 57.5, 56.3.

Example 8

Preparation of 2-(3,5-dihydroxyphenyl)-1-benzofuran-4,6-diol, with the Following Structural Formula

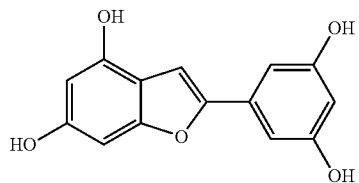 [SMILES: Oc1cc(O)cc(-c2cc3c(O)cc(O)cc3o2)c1]

This compound was prepared using Method A from 3,5-dimethoxyphenol and 2-bromo-1-(3,5-dimethoxyphenyl)ethanone: Yield 74% following procedures A.2 and A.5; m.p. 244° C. (dec.); IR 3349, 2920, 1610, 1442, 1252, 1134 cm$^{-1}$; $^1$H-NMR (500 MHz, δ ppm, DMSO-d$_6$) 9.78 (s, 1H), 9.33 (s, 2H), 9.32 (s, 1H), 7.01 (s, 1H), 6.62 (d, J=2.0, 2H), 6.39 (s, 1H), 6.19-6.15 (m, 2H); $^{13}$C-NMR (126 MHz, δ ppm, CD$_3$OD) 160.0, 158.6, 157.9, 154.5, 152.4, 134.1, 112.9, 103.9, 103.4, 99.8, 98.8, 90.8.

Example 9

Preparation of 2-(4-hydroxyphenyl)-1-benzofuran-4,6-diol, with the Following Structural Formula

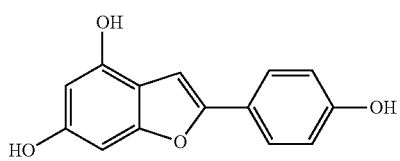

This compound was prepared using Method A from 3,5-dimethoxyphenol and 2-bromo-1-(4-methoxyphenyl)ethanone: Yield 93% following procedures A.2 and A.5; m.p. 216-217° C.; IR 3309, 1613, 1510, 1439, 1241, 1134, 1064 cm$^{-1}$; $^1$H-NMR (500 MHz, δ ppm, DMSO-d$_6$) 9.76 (s, 1H), 9.67 (s, 1H), 9.28 (s, 1H), 7.59 (d, J=8.7 Hz, 2H), 6.97 (s, 1H), 6.83 (d, J=8.7 Hz, 2H), 6.39 (d, J=0.8 Hz, 1H), 6.16 (d, J=1.8 Hz, 1H); $^{13}$C-NMR (126 MHz, δ ppm, CD$_3$OD) 158.7, 158.4, 157.3, 154.8, 152.1, 126.8, 124.3, 116.7, 113.1, 98.8, 97.4, 90.9.

Example 10

Preparation of 2-(4-fluorophenyl)-1-benzofuran-4,6-diol, with the Following Structural Formula

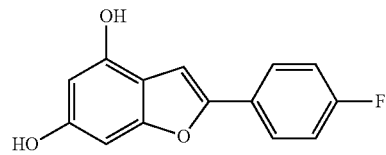 [SMILES: Oc1cc(O)c2cc(-c3ccc(F)cc3)oc2c1]

This compound was prepared using Method A from 3,5-dimethoxyphenol and 2-bromo-1-(4-fluorophenyl)ethanone: Yield 80% following procedures A.2 and A.5; m.p. 189-190° C.; IR 3332, 1614, 1500, 1243, 1125, 1072 cm$^{-1}$; $^1$H-NMR (500 MHz, δ ppm, DMSO-d$_6$) 9.85 (s, 1H), 9.36 (s, 1H), 7.82 (dd, J=8.7 Hz, 5.4 Hz, 2H), 7.27 (t, J=8.9 Hz, 2H), 7.21 (s, 1H), 6.42 (s, 1H), 6.19 (d, J=1.7 Hz, 1H); $^{13}$C-NMR (126 MHz, δ ppm, CD$_3$OD) 163.85 (d, J=246.0 Hz), 158.8, 158.0, 153.3, 152.5, 129.0 (d, J=3.3 Hz), 127.1 (d, J=8.1 Hz), 116.8 (d, J=22.2 Hz), 112.9, 99.7, 98.9, 90.9.

Example 11

Preparation of 5-(4,6-dihydroxy-1-benzofuran-2-yl)benzene-1,2,3-triol, with the Following Structural Formula

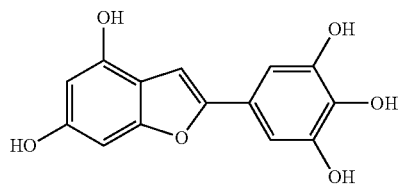 [SMILES: Oc1cc(O)c2cc(-c3cc(O)c(O)c(O)c3)oc2c1]

This compound was prepared using Method A from 3,5-dimethoxyphenol and 2-bromo-1-(3,4,5-trimethoxyphenyl)ethanone: Yield 62% following procedures A.2 and A.5; m.p. 260° C. (dec.); IR 3442, 3326, 1600, 1539, 1470, 1313, 1197, 1072, 1037 cm$^{-1}$; $^1$H NMR (500 MHz, δ ppm, DMSO-d$_6$) 9.67 (s, 1H), 9.22 (s, 1H), 8.97 (s, 2H), 8.29 (s, 1H), 6.81 (s, 1H), 6.69 (s, 2H), 6.37 (s, 1H), 6.14 (s, 1H); $^{13}$C NMR (75 MHz, δ ppm, CD$_3$OD) 158.3, 157.3, 155.0, 151.9, 147.4, 134.8, 123.8, 113.1, 104.8, 98.7, 97.7, 90.8.

Example 12

Preparation of
2-(2,6-dimethoxypyridin-3-yl)benzofuran-4,6-diol,
with the Following Structural Formula

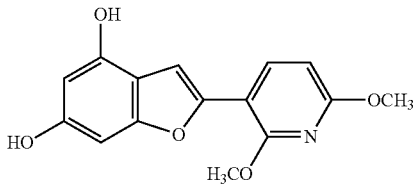 [SMILES: COc1ccc(-c2cc3c(O)cc(O)cc3o2)c(OC)n1]

This compound was prepared using Method A from 3,5-dimethoxyphenol and 2-bromo-1-(2,6-dimethoxypyridin-3-yl)ethanone: Yield 47% following procedures A.2 and A.5; m.p. 97° C. (dec.); IR 3434, 2958, 1587, 1471, 1319, 1265, 1084, 1020 cm$^{-1}$; $^1$H-NMR (500 MHz, δ ppm, DMSO-d$_6$) 9.77 (s, 1H), 9.30 (s, 1H), 8.07 (d, J=8.3 Hz, 1H), 7.13 (s, 1H), 6.51 (d, J=8.3 Hz, 1H), 6.40 (s, 1H), 6.16 (s, 1H), 4.08 (s, 3H), 3.92 (s, 3H); $^{13}$C-NMR (126 MHz, δ ppm, CD$_3$OD) 163.3, 159.7, 157.8, 157.5, 152.3, 149.5, 138.2, 113.3, 107.8, 102.8, 102.6, 98.7, 90.7, 54.1, 54.1.

Example 13

Preparation of
2-(3,5-difluorophenyl)benzofuran-4,6-diol, with the
Following Structural Formula

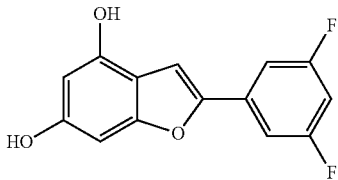 [SMILES: Oc1cc(O)c2cc(-c3cc(F)cc(F)c3)oc2c1]

This compound was prepared using Method A from 3,5-dimethoxyphenol and 2-bromo-1-(3,5-difluorophenyl)ethanone: Yield 60% following procedures A.2 and A.5; m.p. 208-209° C.; IR 3353, 3092, 1615, 1780, 1432, 1349, 1125 cm$^{-1}$; $^1$H-NMR (500 MHz, δ ppm, DMSO-d$_6$) 10.05 (s, 1H), 9.54 (s, 1H), 7.49 (d, J=6.8 Hz, 2H), 7.47 (s, 1H), 7.15 (t, J=8.6 Hz, 1H), 6.43 (s, 1H), 6.21 (s, 1H); $^{13}$C-NMR (126 MHz, δ ppm, CDCl$_3$) 165.1 (dd, J=246.3 Hz, 13.3 Hz), 158.9, 158.9, 152.9, 151.65, 135.7 (t, J=10.6 Hz), 112.7, 107.7 (dd, J=21.0 Hz, 6.8 Hz), 103.3 (t, J=26.1 Hz), 102.6, 99.2, 90.8.

Example 14

Preparation of
3-(3,5-difluorophenyl)-4,6-dimethoxy-1-benzofuran,
with the Following Structural Formula

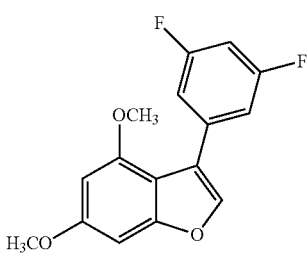 [SMILES: COc1cc(OC)c2c(-c3cc(F)cc(F)c3)coc2c1]

This compound was prepared using Method B from 3,5-dimethoxyphenol and 2-bromo-1-(3,5-difluorophenyl)ethanone: Yield 68% following procedures B.2 and B.3; m.p. 102-103° C.; IR 2937, 1591, 1501, 1444, 1354, 1217, 1113 cm$^{-1}$; $^1$H-NMR (300 MHz, δ ppm, CDCl$_3$) 7.49 (s, 1H), 7.20-7.11 (m, 2H), 6.75 (tt, J=9.0 Hz, 2.3 Hz, 1H), 6.66 (d, J=1.9 Hz, 1H), 6.36 (d, J=1.9 Hz, 1H), 3.84 (s, 3H), 3.82 (s, 3H); $^{13}$C-NMR (75 MHz, δ ppm, CDCl$_3$) 162.8 (dd, J=246.5 Hz, 13.3 Hz), 159.7, 158.2, 154.6, 140.7, 135.8 (t, J=10.6 Hz), 121.5, 112.2 (dd, J=8.1 Hz, 17.4 Hz), 109.2, 102.4 (t, J=25.5 Hz), 95.0, 88.6, 55.9, 55.5.

Example 15

Preparation of
3-(4-hydroxyphenyl)-1-benzofuran-4,6-diol, with the
Following Structural Formula

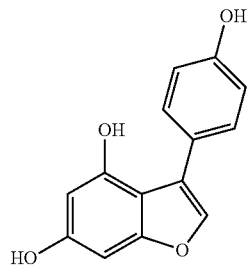 [SMILES: Oc1ccc(-c2coc3cc(O)cc(O)c23)cc1]

This compound was prepared using Method B from 3,5-dimethoxyphenol and 2-bromo-1-(4-methoxyphenyl)ethanone: Yield 38% following procedures B.2, B.3 and B.5; m.p. 220° C. (dec.); IR 3460, 3373, 2914, 1635, 1518, 1229, 1133, 1055 cm$^{-1}$; $^1$H-NMR (500 MHz, δ ppm, DMSO-d$_6$) 9.75 (s, 1H), 9.36 (s, 1H), 9.33 (s, 1H), 7.62 (s, 1H), 7.46 (d, J=8.5 Hz, 2H), 6.75 (d, J=8.5 Hz, 2H), 6.37 (d, J=1.7 Hz, 1H), 6.21 (d, J=1.6 Hz, 1H); $^{13}$C-NMR (126 MHz, δ ppm, CD$_3$OD) 160.2, 157.7, 157.5, 153.6, 139.7, 131.4, 125.4, 124.1, 115.9, 109.6, 99.0, 90.9.

Example 16

Preparation of
3-(3,5-difluorophenyl)-1-benzofuran-4,6-diol, with
the Following Structural Formula

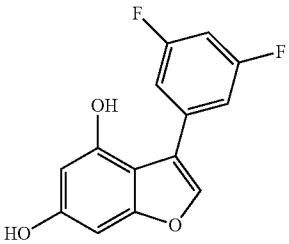 [SMILES: Oc1cc(O)c2c(-c3cc(F)cc(F)c3)coc2c1]

This compound was prepared using Method B from 3,5-dimethoxyphenol and 2-bromo-1-(3,5-difluorophenyl)ethanone: Yield 50% following procedures B.2, B.3 and B.5; m.p. 149-151° C.; IR 3373, 1629, 1507, 1359, 1255, 1157, 1123, 1031 cm$^{-1}$; $^1$H-NMR (500 MHz, δ ppm, DMSO-d$_6$) 10.08 (s, 1H), 9.45 (s, 1H), 8.02 (s, 1H), 7.49 (d, J=7.7 Hz, 2H), 7.13 (t, J=9.4 Hz, 1H), 6.43 (s, 1H), 6.28 (s, 1H); $^{13}$C-NMR (75 MHz, δ ppm, CD$_3$OD) 164.3 (dd, J=244.8 Hz, 13.4 Hz), 160.4, 158.1, 153.5, 141.7, 137.8 (t, J=10.7 Hz), 122.6, 112.8 (dd, J=8.1 Hz, 17.6 Hz), 108.4, 102.6 (t, J=25.9 Hz), 99.4, 91.0.

Example 17

Preparation of 2-bromo-4,6-dimethoxy-3-(4-methoxyphenyl)benzofuran, with the Following Structural Formula

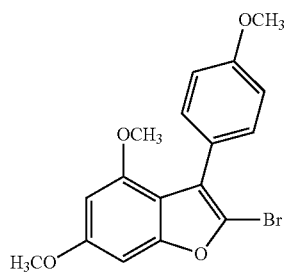 [SMILES: COc1ccc(-c2c(Br)oc3cc(OC)cc(OC)c23)cc1]

This compound was prepared using Method B from 3,5-dimethoxyphenol and 2-bromo-1-(4-methoxyphenyl)ethanone: Yield 83% following procedures B.2, B.3 and B.4; m.p. 125-126° C.; IR 2953, 1629, 1570, 1505, 1245, 1150, 1099, 1034 cm$^{-1}$; $^1$H-NMR (500 MHz, δ ppm, CDCl$_3$) 7.47 (d, J=8.6 Hz, 2H), 6.95 (d, J=8.6 Hz, 2H), 6.62 (s, 1H), 6.31 (s, 1H), 3.85 (s, 3H), 3.83 (s, 3H), 3.71 (s, 3H); $^{13}$C-NMR (126 MHz, δ ppm, CDCl$_3$) 159.2, 159.2, 157.3, 153.9, 131.7, 123.8, 122.9, 120.4, 113.3, 111.6, 95.1, 88.3, 55.9, 55.6, 55.4.

Example 18

Preparation of 2-iodo-4,6-dimethoxy-3-(4-methoxyphenyl)benzofuran, with the Following Structural Formula

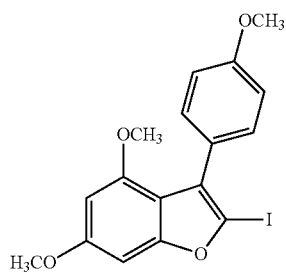 [SMILES: COc1ccc(-c2c(I)oc3cc(OC)cc(OC)c23)cc1]

This compound was prepared using Method B from 3,5-dimethoxyphenol and 2-bromo-1-(4-methoxyphenyl)ethanone: Yield 81% following procedures B.2, B.3 and B.4; $^1$H-NMR (200 MHz, δ ppm, CDCl$_3$) 7.43 (d, J=8.7 Hz, 2H), 6.95 (d, J=8.7 Hz, 2H), 6.64 (d, J=1.8 Hz, 1H), 6.28 (d, J=1.8 Hz, 1H), 3.86 (s, 3H), 3.83 (s, 3H), 3.70 (s, 3H).

Example 19

Preparation of 3-(4-fluorophenyl)benzofuran-4,6-diol, with the Following Structural Formula

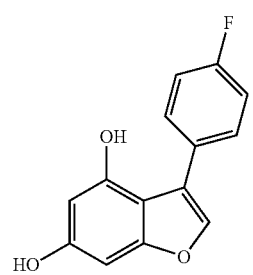 [SMILES: Oc1cc(O)c2c(-c3ccc(F)cc3)coc2c1]

This compound was prepared using Method B from 3,5-dimethoxyphenol and 2-bromo-1-(4-fluorophenyl)ethanone: Yield 27% following procedures B.2, B.3 and B.5; m.p. 125° C. (dec.); IR 3508, 1612, 1508, 1455, 1240, 1121, 1090, 1048 cm$^{-1}$; $^1$H-NMR (500 MHz, δ ppm, DMSO-d$_6$) 9.84 (s, 1H), 9.36 (s, 1H), 7.77 (s, 1H), 7.70 (dd, J=8.1 Hz, 5.9 Hz, 2H), 7.20 (t, J=8.8 Hz, 2H), 6.41 (s, 1H), 6.25 (s, 1H); $^{13}$C NMR (126 MHz, δ ppm, CD$_3$OD) 163.7 (d, J=243.9 Hz), 160.2, 157.7, 153.6, 140.4, 132.0 (d, J=7.9 Hz), 130.4 (d, J=3.3 Hz), 123.3, 115.6 (d, J=21.6 Hz), 109.2, 99.1, 91.0.

Example 20

Preparation of 2-bromo-3-(3,5-difluorophenyl)benzofuran-4,6-diol, with the Following Structural Formula

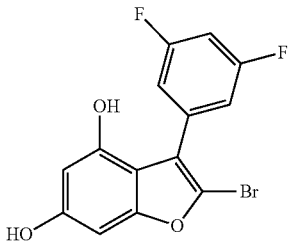 [SMILES: Oc1cc(O)c2c(-c3cc(F)cc(F)c3)c(Br)oc2c1]

This compound was prepared using Method B from 3,5-dimethoxyphenol and 2-bromo-1-(3,5-difluorophenyl)ethanone: Yield 14% following procedures B.2, B.3 and B.5; m.p. 121-122° C.; IR 3379, 1620, 1591, 1429, 1121, 1069 cm$^{-1}$; $^1$H-NMR (500 MHz, δ ppm, DMSO-d$_6$) 9.25 (s, 1H), 9.24 (s, 1H), 7.02 (t, J=8.8 Hz, 1H), 6.72 (d, J=6.4 Hz, 2H), 6.28 (s, 1H), 6.06 (s, 1H); $^{13}$C NMR (126 MHz, δ ppm, CDCl$_3$) 163.4 (dd, J=246.0 Hz, 13.4 Hz), 157.5, 156.7, 154.7, 153.2, 139.3 (t, J=10.6 Hz), 115.8, 114.9 (dd, J=7.5 Hz, 17.0 Hz), 112.0, 102.8 (t, J=25.6 Hz), 98.9, 90.4.

Biological Assays

Compounds according to the present invention are modulators of sirtuins.

Some of the compounds of the present invention are inhibitors of the enzyme SIRT1. The inhibitory activity is measured as the concentration of compound required to reduce the enzyme activity by 50% (IC50).

Some other compounds of the present invention are activators of the enzyme SIRT1. Activation in this assay is measured both as the concentration of compound required to increase the enzyme activity by 50% (EC1.5) as well as by the percentage of maximum activation achieved (Max %) (see, FIG. 1).

Example 21

In Vitro Biological Activity

50 μM of substrate peptide (acetylated AMC-labeled peptide from p53 residues 379-382, RHKKAc, BioMol. Cat. #KI-177), 91 nM of human SIRT1 (full length human Sirtuin 1 expressed in E. coli, BioMol. Cat. #SE-239) and 500 μM NAD$^+$ in the assay buffer (50 mM Tris-HCl, pH 8.0, 137 mM NaCl, 2.7 mM KCl, 1 mM MgCl$_2$ supplemented with 1 mg/ml BSA for dilution, BioMol. Cat. #KI-143) and 1% final concentration of DMSO were incubated in the presence of gradient concentrations of test compounds (10-dose with 3-fold serial dilution) at 30° C. for 2 h. The reactions were carried out in a 96-well microplate for fluorometry in a 50 μl reaction volume. After the deacetylation reaction, Fluor-de-Lys-Developer II (BioMol. Cat. #KI-176) was added to each well to digest the deacetylated substrate, thus producing the fluorescent signal. The reaction was allowed to develop for 45 minutes at 30° C. with 5% CO$_2$; then the fluorescent signal was measured with an excitation wavelength at 360 nm and an emission wavelength at 460 nm in a microplate-reading fluorometer (GeminiXS; Molecular Devices, Sunnyvale, Calif.). A curve of Deacetylated Standard (Biomol, Cat. #KI-142; made from 100 μM with 1:2 dilution and 10-doses, 6 μl) allowed the conversion of fluorescent signal into micromoles of deacetylated product. All experiments were performed in triplicate. DMSO was used as negative control; Suramin sodium (Biomol Cat. #G-430) was used as inhibition positive control and resveratrol (Biomol Cat. #FR-104) as activation positive control.

SIRT1 Inhibitors:

| Compound | IC50 (μM) |
|---|---|
| Suramin | 2.62 |
| Example 11 | 1.84 |
| Example 13 | 36.7 |
| Example 15 | 22.8 |
| Example 16 | 274 |
| Example 19 | 192 |
| Example 20 | 76.3 |

SIRT1 Activators:

| Compound | EC1.5 (nM) | Max (%) |
|---|---|---|
| Resveratrol | 12.3 | 474.65 |
| Example 8 | 1.32 | 406.85 |
| Example 9 | 3.55 | 443.52 |
| Example 10 | 13.49 | 278.8 |
| Example 12 | — | 130.17 |
| 5-(6-hydroxy-1-benzofuran-2-yl)benzene-1,3-diol (Comparative) | 11.48 | 450.78 |

The invention claimed is:

1. Compounds of general formula (I),

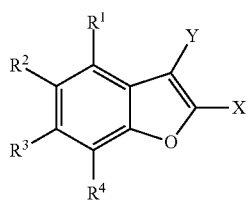

(I)

wherein:
$R^1$ and $R^3$ are hydroxyl;
$R^2$ and $R^4$ are, independently of each other, selected from the group consisting of alkoxy of linear or branched alkyl chain, hydrogen, halogen, nitro, cyano and hydroxyl, or wherein either pair $R^1R^2$, $R^2R^3$ or $R^3R^4$ together form a phenyl group;
one of X and Y is hydrogen, $C_1$-$C_3$ alkyl, or halogen; and the other one is a group of formula (V):

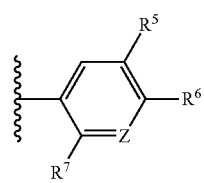

(V)

wherein:
$R^5$ and $R^7$ are, independently of each other, selected from the group consisting of hydrogen, halogen, hydroxy, nitro, cyano and alkoxy of linear or branched alkyl chain, $R^6$ is selected from the group consisting of —F, hydroxyl, —O—($C_1$-$C_3$ alkyl), nitro, and cyano,
Z represents a —(C=$R^8$)— group wherein, $R^8$ is selected from the group consisting of hydrogen, hydroxyl, nitro, cyano and alkoxy of linear or branched alkyl chain;
with the proviso that at least two of $R^1$, $R^2$, $R^3$, $R^4$, $R^5$, $R^6$, $R^7$ or $R^8$ are hydroxyl or alkoxy group of linear or branched alkyl chain;
and with the proviso that at least three of $R^1$, $R^2$, $R^3$, $R^4$, $R^5$, $R^6$, $R^7$ or $R^8$ are not hydrogen;
or a salt thereof.

2. Compound according to claim 1, wherein each alkoxy group of linear or branched alkyl chain is independently selected from —O—$C_1$-$C_3$ alkyl.

3. Compound according to claim 1, selected from the group consisting of:
2-(4-hydroxyphenyl)-1-benzofuran-4,6-diol
2-(4-fluorophenyl)-1-benzofuran-4,6-diol
5-(4,6-dihydroxy-1-benzofuran-2-yl)benzene-1,2,3-triol
3-(4-hydroxyphenyl)-1-benzofuran-4,6-diol
3-(4-fluorophenyl)benzofuran-4,6-diol
or a salt thereof.

4. Compound according to claim 1, selected from the group consisting of
2-(4-Hydroxyphenyl)-1-benzofuran-4,6-diol, with the following structural formula:

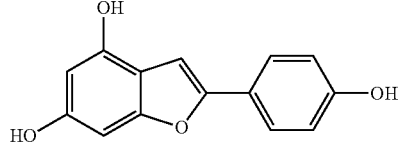 [SMILES: Oc1ccc(-c2cc3c(O)cc(O)cc3o2)cc1]

2-(4-Fluorophenyl)-1-benzofuran-4,6-diol, with the following structural formula:

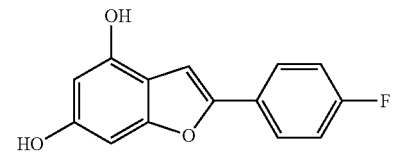 [SMILES: Oc1cc(O)c2cc(-c3ccc(F)cc3)oc2c1]

5-(4,6-Dihydroxy-1-benzofuran-2-yl)benzene-1,2,3-triol, with the following structural formula:

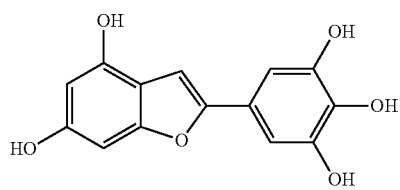 [SMILES: Oc1cc(O)c2cc(-c3cc(O)c(O)c(O)c3)oc2c1]

3-(4-Hydroxyphenyl)-1-benzofuran-4,6-diol, with the following structural formula:

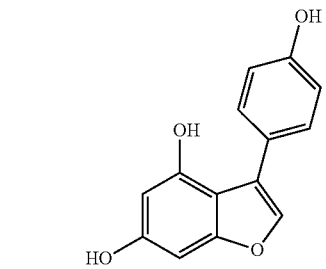 [SMILES: Oc1ccc(-c2coc3cc(O)cc(O)c23)cc1]

or a salt thereof.

5. Process for the preparation of a compound of general formula (Ia):

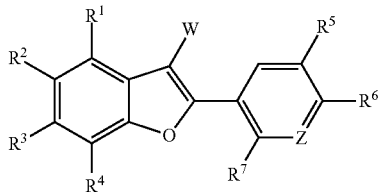

(Ia)

wherein $R^1$, $R^2$, $R^3$, $R^4$, $R^5$, $R^6$, $R^7$ and Z have the meaning given in claim 1;
and wherein $R^1$ and $R^3$ are hydroxyl groups when Z is —(C—$R^8$)—;
with the proviso that at least two of $R^1$, $R^2$, $R^3$, $R^4$, $R^5$, $R^6$, $R^7$ or $R^8$ are hydroxyl or alkoxy group of linear or branched alkyl chain;
and with the proviso that at least three of $R^1$, $R^2$, $R^3$, $R^4$, $R^5$, $R^6$, $R^7$ or $R^8$ are not hydrogen;
and W can be a hydrogen atom or a halogen atom or a $C_1$-$C_3$ alkyl group, which comprises reacting a mixture of materials a), b), c) and d):
a) a compound of formula (IIa)

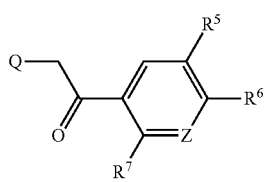

(IIa)

wherein Q can be a chlorine, bromine or iodine atom, or a leaving group such as mesylate or tosylate, Z has the meaning given above, except for —(C—OH)—, and $R^5$, $R^6$ and $R^7$ have the meaning given above, except for hydroxyl group;
b) a compound of general formula (III),

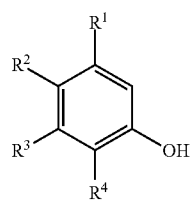

(III)

wherein $R^1$ and $R^3$ are, independently of each other, selected from the group consisting of alkoxy of linear or branched alkyl chain,
$R^2$ and $R^4$ have the meaning given above, except for hydroxyl group;
c) neutral alumina; and
d) a solvent
and optionally performing one or more of the reactions selected from the group consisting of: (i) deprotecting any alkoxy groups to obtain the corresponding hydroxylated products; (ii) halogenating; and (iii) alkylating;

characterized in that said mixture of materials a), b), c) and d) is treated with microwaves and does not include a base.

6. Process for the preparation of a compound of general formula (Ib):

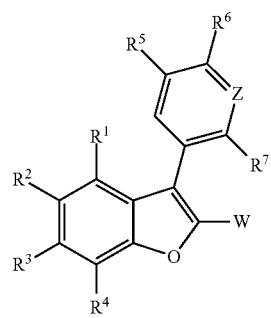

(Ib)

wherein $R^1$, $R^2$, $R^3$, $R^4$, $R^5$, $R^6$, $R^7$ and Z have the meaning given in claim 1;
and wherein $R^1$ and $R^3$ are hydroxyl groups when Z is —(C—$R^8$)—;
with the proviso that at least two of $R^1$, $R^2$, $R^3$, $R^4$, $R^5$, $R^6$, $R^7$ or $R^8$ are hydroxyl or alkoxy group of linear or branched alkyl chain;
and with the proviso that at least three of $R^1$, $R^2$, $R^3$, $R^4$, $R^5$, $R^6$, $R^7$ or $R^8$ are not hydrogen;
and W the meaning given in claim 5, which comprises reacting a mixture of materials a), b), and c):
a) a compound of formula (IIb)

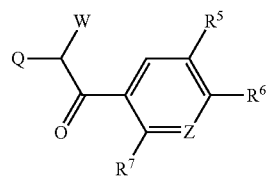

(IIb)

wherein $R^5$, $R^6$, $R^7$ and Z have the meaning given in claim 1 and W and Q the meaning given in claim 5;
b) a compound of general formula (III), as defined in claim 5, and
c) a base and an organic solvent,
to obtain a compound of general formula (IV):

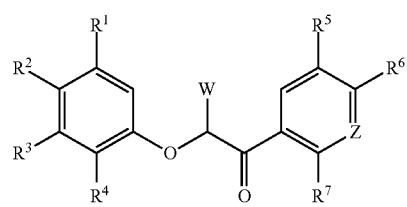

(IV)

and further reacting the obtained product (IV) with alumina to obtain benzofuranes of general formula (Ib);
and optionally performing one or more of the reactions selected from the group consisting of: (i) deprotecting any alkoxy groups to obtain the corresponding hydroxylated products; (ii) halogenating; and (iii) alkylating.

7. A pharmaceutical composition that comprises at least a compound of formula (I) as defined in claim 1, or a pharmaceutically acceptable salt thereof, and at least a pharmaceutically acceptable excipient.

* * * * *

UNITED STATES PATENT AND TRADEMARK OFFICE
CERTIFICATE OF CORRECTION

PATENT NO. : 8,835,659 B2  Page 1 of 1
APPLICATION NO. : 13/695971
DATED : September 16, 2014
INVENTOR(S) : Cossio Mora et al.

It is certified that error appears in the above-identified patent and that said Letters Patent is hereby corrected as shown below:

On the Title Page item (75), Inventor 3: change "Yosu Ion Vara Zalazar" to --Yosu Ion Vara Salazar--

Signed and Sealed this
Fourteenth Day of April, 2015

Michelle K. Lee
*Director of the United States Patent and Trademark Office*